United States Patent
Schumacher et al.

(10) Patent No.: US 11,447,491 B2
(45) Date of Patent: *Sep. 20, 2022

(54) ALDOSTERONE SYNTHASE INHIBITOR

(71) Applicant: DAMIAN PHARMA AG, Walchwil (CH)

(72) Inventors: Christoph Schumacher, Walchwil (CH); Walter Fuhrer, Lupsingen (CH); Ronald Edward Steele, Long Valley, NJ (US)

(73) Assignee: DAMIAN PHARMA AG, Walchwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/991,856

(22) Filed: Aug. 12, 2020

(65) Prior Publication Data

US 2021/0024519 A1 Jan. 28, 2021

Related U.S. Application Data

(63) Continuation of application No. 16/345,209, filed as application No. PCT/EP2017/077511 on Oct. 26, 2017, now Pat. No. 10,822,332.

(60) Provisional application No. 62/413,635, filed on Oct. 27, 2016.

(30) Foreign Application Priority Data

Dec. 19, 2016 (EP) ..................... 16205019

(51) Int. Cl.
*C07D 471/04* (2006.01)
*A61P 9/00* (2006.01)
*A61P 9/12* (2006.01)
*A61P 13/12* (2006.01)
*A61K 31/437* (2006.01)

(52) U.S. Cl.
CPC .......... *C07D 471/04* (2013.01); *A61K 31/437* (2013.01); *A61P 9/00* (2018.01); *A61P 9/12* (2018.01); *A61P 13/12* (2018.01)

(58) Field of Classification Search
CPC .. C07D 471/04; A61P 9/00; A61P 9/12; A61P 13/12; A61K 31/437
See application file for complete search history.

(56) References Cited

U.S. PATENT DOCUMENTS

| | | | |
|---|---|---|---|
| 5,098,911 A | 3/1992 | Ibrahim | |
| 5,428,160 A * | 6/1995 | Browne | C07D 213/38 544/61 |
| 10,822,332 B2 * | 11/2020 | Schumacher | A61P 9/12 |

FOREIGN PATENT DOCUMENTS

| | | |
|---|---|---|
| EP | 1886695 A1 | 2/2008 |
| WO | 2001/076574 A2 | 10/2001 |
| WO | 2005/099695 A1 | 10/2005 |
| WO | 2007/024945 A1 | 3/2007 |
| WO | 2013/109514 A1 | 7/2013 |

OTHER PUBLICATIONS

International Search Report issued in International Application No. PCT/EP2017/077511, dated Nov. 27, 2017.
Azizi et al., "Aldosterone synthase inhibition in humans," Nephrology Dialysis Transplantation 28(1):36-43 (2013).
Fiebeler et al., "Aldosterone Synthase Inhibitor Ameliorates Angiotensin II-Induced Organ Damage," Circulation 111:3087-3094 (2005).
Furet et al., "Aromatase Inhibitors: Synthesis, Biological Activity, and Binding Mode of Azole-Type Compounds," J. Med. Chem. 36:1393-1400 (1993).
Hojo et al., "Adult male rat hippocampus synthesizes estradiol from pregnenolone by cytochromes P45017α and P450 aromatase localized in neurons," Proceedings of the National Academy of Sciences 101(3):865-870 (2004).
Kandasamy et al., "Possible Existence of the Hypothalamic-Pituitary-Hippocampal (HPH) Axis: A Reciprocal Relationship Between Hippocampal Specific Neuroestradiol Synthesis and Neuroblastosis in Ageing Brains with Special Reference to Menopause and Neurocognitive Disorders," Neurochemical Research 44:1781-1795 (2019).
Martin et al., "Discovery of 4-Aryl-5,6,7,8-tetrahydroisoquinolines as Potent, Selective, and Orally Active Adosterone Synthase (CYP11 B2) Inhibitors: In Vivo Evaluation in Rodents and Cynomolgus Monkeys," Journal of Medicinal Chemistry 58:8054-8065 (2015).
Ménard et al., "Can the dextroenantiomer of the aromatase inhibitor fadrozole be useful for clinical investigation of aldosterone-synthase inhibition?" Journal of Hypertension 24(6):993-7 (2006).
Ménard et al., "Investigation of aldosterone-synthase inhibition in rats," Journal of Hypertension 24(6):1147-1155 (2006).
Minnaard-Huiban et al., "Fadrozole reverses cardiac fibrosis in spontaneously hypertensive heart failure rats: discordant enantioselectivity versus reduction of plasma aldosterone," Endocrinology 149(1):28-31 (2008).

(Continued)

*Primary Examiner* — Timothy R Rozof
(74) *Attorney, Agent, or Firm* — Medler Ferro Woodhouse & Mills PLLC

(57) ABSTRACT

The present invention relates to a compound selected from (R)-(+)-5-(p-cyanophenyl)-5,6,7,8-tetrahydroimidazo[1,5-a]pyridine and a pharmaceutically acceptable salt thereof, and in particular to the phosphate salt of (R)-(+)-5-(p-cyanophenyl)-5,6,7,8-tetrahydroimidazo[1,5-a]pyridine, both having preferably an enantiomeric excess of the (R) form higher than or equal to 97%. Furthermore, the present invention relates to pharmaceutical compositions comprising the same, their use as a medicament and in methods of treatment of diseases and disorders in humans including women of child bearing potential and pediatric patients in which aldosterone over-exposure contributes to the deleterious effects of said diseases or disorders, as well as processes for preparing said inventive compounds.

28 Claims, 7 Drawing Sheets

(56) References Cited

OTHER PUBLICATIONS

Roumen et al., "Construction of 3D Models of the CYP11B Family as a Tool to Predict Ligand Binding Characteristics" J Comput Aided Mol Des 21(8):455-471 (2007).

* cited by examiner

ALDOSTERONE SYNTHASE INHIBITOR

The present invention relates to a compound selected from (R)-(+)-5-(p-cyanophenyl)-5,6,7,8-tetrahydroimidazo[1,5-a]pyridine and a pharmaceutically acceptable salt thereof, and in particular to the phosphate salt of (R)-(+)-5-(p-cyanophenyl)-5,6,7,8-tetrahydroimidazo[1,5-a]pyridine, both having preferably an enantiomeric excess of the (R) form higher than or equal to 97%. Furthermore, the present invention relates to pharmaceutical compositions comprising the same, their use as a medicament and in methods of treatment of diseases and disorders in which aldosterone over-exposure contributes to the deleterious effects of said diseases or disorders including in premenopausal women and pediatric patients, as well as processes for preparing said inventive compounds.

RELATED ART

Aldosterone synthase (CYP11B2) inhibition has emerged as a new option for the treatment of hypertension, heart failure and renal disorders, in addition to mineralocorticoid receptor (MR) blockade. The aim is to decrease aldosterone concentrations in both plasma and tissues, thereby decreasing MR-dependent and MR-independent effects in the cardiac, vascular and renal target organs. Aldosterone is produced in the zona glomerulosa of the adrenal gland by the enzymatic action of aldosterone synthase (CYP11B2) on deoxycorticosterone (M. Azizi et al., Nephrol Dial Transplant (2013) 28: 36-43).

Initial attempts to inhibit aldosterone synthesis involved the use of various non-selective inhibitors of steroidogenesis but the same was a major safety concern. The concept of targeted pharmacological approach to the specific inhibition of aldosterone synthesis was initiated by the discovery that fadrozole hydrochloride (CGS16949A, INN: Fadrozole; U.S. Pat. Nos. 4,617,307; 4,728,645; 5,098,911), known as a non-steroidal aromatase inhibitor effective for advanced breast cancer treatment, affected aldosterone levels. Subsequent preclinical studies demonstrated that the R-enantiomer (R)-(+)-5-(p-cyanophenyl)-5,6,7,8-tetrahydroimidazolium[1,5-a]pyridine chloride is a potent inhibitor of CYP11B2 while the S-enantiomer is responsible for the strong and potent aromatase (CYP19) inhibiting activity of CGS16949A (J. Ménard et al., J Hypertens (2006) 24:993; Fiebeler et al., Circulation (2005) 111:3078-94; Furet et al., J Med Chem (1993) 36:1393-1400; U.S. Pat. No. 5,057,521).

On the other hand, and despite its early discovery, clinical development of (R)-(+)-5-(p-cyanophenyl)-5,6,7,8-tetrahydroimidazolium[1,5-a]pyridine chloride in humans has never been reported and neither a commercially viable synthesis nor a satisfying chiral purity has been disclosed (U.S. Pat. No. 4,889,861). In addition, (R)-(+)-5-(p-cyanophenyl)-5,6,7,8-tetrahydroimidazolium[1,5-a]pyridine chloride has been found to be highly hygroscopic (Browne L J et al., J Med Chem (1991) 34:725-36; Furet et al., J Med Chem (1993) 36:1393-1400; U.S. Pat. No. 4,889,861).

The chiral purity of (R)-(+)-5-(p-cyanophenyl)-5,6,7,8-tetrahydroimidazolium[1,5-a]pyridine chloride is in particular of importance in light of the strong and potent aromatase inhibiting activity of the corresponding (S) enantiomer since extensive evaluation of aromatase inhibitors in clinical trials has revealed numerous deleterious consequences of aromatase inhibition. Thus, a systematic review and meta-analysis consisting of seven trials in 30,023 postmenopausal women with breast cancer and treated with aromatase inhibitors revealed significant increases in the occurrence of bone fractures and cardiovascular disease (Amir et al., J Natl Cancer Inst (2011) 103:1299-1309). Furthermore, the longer the duration of aromatase inhibition, the stronger the association with cardiovascular disease and bone fractures. In addition, in premenopausal women i.e. in women of child bearing potential, exposure to aromatase inhibition may lead to reproduction disorders and in lactating women, newborns may be exposed to aromatase-inhibiting compounds via secretion into the breast milk. Further, in pediatric patients aromatase inhibition may lead to developmental disorders. Thus, the need for a very high purity and avoidance of contaminants and impurities of such drugs, which are usually applied for a long period of time or even for lifetime, is evident.

Moreover, and beside the required very high chiral purity and the avoidance of aromatase inhibition as an adverse effect, solubility in water and stability including enantiomeric stability over an extended period of time in order to exclude any conversion to aromatase-inhibiting moieties, as well as the processability of such a drug, particularly into forms of administration suitable of oral administration such as tablets, are further combined prerequisites for a pharmaceutical preparation of such a drug.

SUMMARY OF THE INVENTION

The inventors have now surprisingly provided (R)-(+)-5-(p-cyanophenyl)-5,6,7,8-tetrahydroimidazo[1,5-a]pyridine of formula (I) with an unprecedented degree of chiral purity i.e., enantiomeric excess (ee), typically and preferably having an ee of the (R) form higher than or equal to 97%, further preferably even with an ee of the (R) form higher than or equal to 99% or even higher than or equal to 99.5%. Moreover, the inventors have further surprisingly found that the phosphate salt of (R)-(+)-5-(p-cyanophenyl)-5,6,7,8-tetrahydroimidazo[1,5-a]pyridine, and in particular (R)-(+)-5-(p-cyanophenyl)-5,6,7,8-tetrahydroimidazolium[1,5-a]pyridine dihydrogen phosphate, is non-hygroscopic and stable over an extended period of time, in particular with respect to purity, water content as well as enantiomeric purity. Furthermore and importantly, the inventors have surprisingly found that the phosphate salt of (R)-(+)-5-(p-cyanophenyl)-5,6,7,8-tetrahydroimidazo[1,5-a]pyridine, and in particular (R)-(+)-5-(p-cyanophenyl)-5,6,7,8-tetrahydroimidazolium[1,5-a]pyridine dihydrogen phosphate is crystalline in one stable form. In addition, the inventive compounds furthermore possess a decreased and very low aromatase activity, and consequently an increased and very high aldosterone synthase activity, which makes the inventive compounds very suitable as candidates for clinical development in humans, in particular for premenopausal women and pediatric patients. The very low aromatase activity is believed to be even a prerequisite for clinical development and registered use as a medicament to treat diseases and disorders associated with aldosterone overexposure, in particular for premenopausal women, and thus women of child bearing potential, and pediatric patients. The latter is in particular true since and although the amount of aromatase and the percentage conversion of androgen to estrogen may be quantitatively small in extra-gonadal tissues, often being below 1% in any tissue, the effects in terms of hormonal action still may be great (Blakemore and Nafiolin, Physiology (2016) 31:258-269). Thus, the inventive compounds provide for the possibility of life-time treatment of disorders negatively affected by aldosterone production due to minimizing the contamination and negative and unwanted effects caused by the potent aromatase inhibiting (S)-enantiomer.

Accordingly, in a first aspect, the present invention provides for a compound selected from (R)-(+)-5-(p-cyanophenyl)-5,6,7,8-tetrahydroimidazo[1,5-a]pyridine of formula (I) and a pharmaceutically acceptable salt thereof, wherein said compound has an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9%.

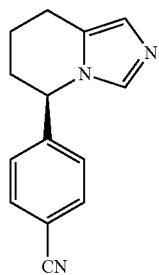

(I)

In particular, and in a second aspect, the present invention provides for (R)-(+)-5-(p-cyanophenyl)-5,6,7,8-tetrahydroimidazolium[1,5-a]pyridine dihydrogen phosphate, typically and preferably having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9% and which has been surprisingly found to be non-hygroscopic and stable over an extended period of time, and hereby in particular with respect to purity, water content and chiral purity. This in particular important since hygroscopicity typically affects negatively the stability of the active pharmaceutical ingredient. Furthermore and importantly, the phosphate salt of (R)-(+)-5-(p-cyanophenyl)-5,6,7,8-tetrahydroimidazo[1,5-a]pyridine, and in particular (R)-(+)-5-(p-cyanophenyl)-5,6,7,8-tetrahydroimidazolium[1,5-a]pyridine dihydrogen phosphate is crystalline in one stable form. Unstable polymorphic forms typically affect negatively pharmaceutical efficacy properties.

Furthermore, the present invention provides in further aspects for (R)-(+)-5-(p-cyanophenyl)-5,6,7,8-tetrahydroimidazo[1,5-a]pyridine as well as the phosphate salt thereof, preferably the (R)-(+)-5-(p-cyanophenyl)-5,6,7,8-tetrahydroimidazolium[1,5-a]pyridine dihydrogen phosphate, typically and preferably having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9%, for use as a medicament and for use in a method of the treatment of a disease or disorder in humans including women of child bearing potential and pediatric patients, in which aldosterone over-exposure contributes to the deleterious effects of said disease or disorder, wherein said disease or disorder is typically and preferably selected from primary and secondary hyperaldosteronism, heart failure, chronic renal failure, hypertension, restenosis, obesity, nephropathy, post-myocardial infarction, renal fibrosis, and coronary heart disease; and wherein further preferably said disease or disorder is selected from primary and secondary hyperaldosteronism.

Further preferably, said method is in particular suited for use in humans including preferably for women of child bearing potential and pediatric patients.

The achieved inventive chiral resolution and synthesis of (R)-(+)-5-(p-cyanophenyl)-5,6,7,8-tetrahydroimidazo[1,5-a]pyridine and (R)-(+)-5-(p-cyanophenyl)-5,6,7,8-tetrahydroimidazolium[1,5-a]pyridine dihydrogen phosphate in such a high chiral purity allows now the preparation of pharmaceutical compositions for suppression of aldosterone, typically and preferably by inhibiting the rate limiting enzyme in aldosterone synthesis, namely aldosterone synthase (CYP11B2), with least possible unwanted contaminating aromatase activity. The typical need for life-time treatment of said diseases and disorders reinforces the advantages of the present invention in minimizing the contamination of the beneficial aldosterone synthase inhibiting (R)-(+)-5-(p-cyanophenyl)-5,6,7,8-tetrahydroimidazo[1,5-a]pyridine or a pharmaceutically acceptable salt thereof, and hereby in particular the phosphate salt thereof, and further preferably the (R)-(+)-5-(p-cyanophenyl)-5,6,7,8-tetrahydroimidazolium[1,5-a]pyridine dihydrogen phosphate, from the potent aromatase inhibiting (S)-(−)-enantiomer. As presented in Example 8, Tables 10 and 11, the inventive phosphate salt of (R)-(+)-5-(p-cyanophenyl)-5,6,7,8-tetrahydroimidazo[1,5-a]pyridine, preferably the (R)-(+)-5-(p-cyanophenyl)-5,6,7,8-tetrahydroimidazolium[1,5-a]pyridine dihydrogen phosphate, inhibits aldosterone production (aldosterone synthase activity) and estradiol production (aromatase activity) by NCI-H295R adrenal cells with $IC_{50}$'s of 8.1 nM and 5760 nM, respectively; thus demonstrating a more than 700-fold greater inhibition of aldosterone synthase activity as compared to aromatase activity evidencing a highly beneficial safety profile for the inventive phosphate salt of (R)-(+)-5-(p-cyanophenyl)-5,6,7,8-tetrahydroimidazo[1,5-a]pyridine, and further the (R)-(+)-5-(p-cyanophenyl)-5,6,7,8-tetrahydroimidazolium[1,5-a]pyridine dihydrogen phosphate. Thus, the present invention is in particular suited for application in humans, in particular for premenopausal women and pediatric patients. The very low aromatase activity is believed to be even a prerequisite for clinical development and use as a medicament for aldosterone-associated diseases and disorders, in particular for premenopausal women, and thus women of child bearing potential, and pediatric patients.

The inventors have found that (R)-(+)-5-(p-cyanophenyl)-5,6,7,8-tetrahydroimidazo[1,5-a]pyridine prepared by the process of the invention, as well as its phosphate salt, in particular the (R)-(+)-5-(p-cyanophenyl)-5,6,7,8-tetrahydroimidazolium[1,5-a]pyridine dihydrogen phosphate, exhibit an unprecedented low inhibitory activity for aromatase. Accordingly, in a further aspect, the present invention provides for (R)-(+)-5-(p-cyanophenyl)-5,6,7,8-tetrahydroimidazo[1,5-a]pyridine or a pharmaceutically acceptable salt thereof, in particular the phosphate salt thereof, more preferably the (R)-(+)-5-(p-cyanophenyl)-5,6,7,8-tetrahydroimidazolium[1,5-a]pyridine dihydrogen phosphate, having an $IC_{50}$ value for aromatase higher than or equal to 700 nM determined by the cell-free human recombinant aromatase enzyme assay described in Example 8, in which the phosphate salt of (R)-(+)-5-(p-cyanophenyl)-5,6,7,8-tetrahydroimidazo[1,5-a]pyridine, preferably the (R)-(+)-5-(p-cyanophenyl)-5,6,7,8-tetrahydroimidazolium[1,5-a]pyridine dihydrogen phosphate, was found to inhibit aromatase activity with an $IC_{50}$ of 1640 nM.

Moreover, the inventors have found that (R)-(+)-5-(p-cyanophenyl)-5,6,7,8-tetrahydroimidazo[1,5-a]pyridine prepared by the process of the invention, as well as its phosphate salt, preferably the (R)-(+)-5-(p-cyanophenyl)-5,6,7,8-tetrahydroimidazolium[1,5-a]pyridine dihydrogen phosphate, exhibit an unprecedented high inhibitory activity for aldosterone synthase. Accordingly, in a further aspect, the present invention provides for a compound selected from (R)-(+)-5-(p-cyanophenyl)-5,6,7,8-tetrahydroimidazo[1,5-a]pyridine and a pharmaceutically acceptable salt thereof, in particular the phosphate salt thereof, more preferably the (R)-(+)-5-(p-cyanophenyl)-5,6,7,8-tetrahydroimidazolium[1,5-a]pyridine dihydrogen phosphate, wherein said compound inhibits aldosterone synthase in the NCI-H295R adrenal cell assay described in Example 8 with an $IC_{50}$ of 100 nM or less.

In a further aspect, the present invention provides for a process for preparing a compound selected from (R)-(+)-5-(p-cyanophenyl)-5,6,7,8-tetrahydroimidazo[1,5-a]pyridine and a pharmaceutically acceptable salt thereof characterized by enantioselective crystallization of the (−)-O,O'-dibenzoyl-L-tartaric acid salt of (R)-(+)-5-(p-cyanophenyl)-5,6,7,8-tetrahydroimidazo[1,5-a]pyridine, and wherein very preferably said pharmaceutically acceptable salt is the dihydrogen phosphate thereof.

In a further aspect, the present invention provides for a compound selected from (R)-(+)-5-(p-cyanophenyl)-5,6,7,8-tetrahydroimidazo[1,5-a]pyridine and a pharmaceutically acceptable salt thereof, wherein said compound has a specific optical rotation $[\alpha]_D^{20}$ ($CH_3CN:H_2O$ 1:1 (v/v)), $[\alpha]_D^{20}$ (ethanol) or $[\alpha]_D^{25}$ (ethanol), preferably $[\alpha]_D^{20}$ ($CH_3CN:H_2O$ 1:1 (v/v)), of at least +95°, preferably of at least +96°, more preferably of at least +97°, even more preferably of at least +98°, and wherein preferably said compound is (R)-(+)-5-(p-cyanophenyl)-5,6,7,8-tetrahydroimidazolium[1,5-a]pyridine dihydrogen phosphate, and wherein further preferably said compound inhibits aromatase activity in the cell-free human recombinant aromatase enzyme assay described in Example 8 with an $IC_{50}$ of 700 nM or more, preferably 1000 nM or more, and more preferably 1500 nM or more; and wherein again further preferably said compound inhibits aldosterone synthase in the NCI-H295R adrenal cell assay described in Example 8 with an $IC_{50}$ of 100 nM or less, preferably 50 nM or less, and more preferably 10 nM or less. In a very preferred embodiment, said compound is (R)-(+)-5-(p-cyanophenyl)-5,6,7,8-tetrahydroimidazolium[1,5-a]pyridine dihydrogen phosphate and has a specific optical rotation $[\alpha]_D^{20}$ ($CH_3CN:H_2O$ 1:1 (v/v)) of at least +95°, preferably of at least +96°, more preferably of at least +97°, even more preferably of at least +98°, and wherein preferably said compound inhibits aromatase activity in the cell-free human recombinant aromatase enzyme assay described in Example 8 with an $IC_{50}$ of 700 nM or more, preferably 1000 nM or more, and more preferably 1500 nM or more; and wherein further preferably said compound inhibits aldosterone synthase in the NCI-H295R adrenal cell assay described in Example 8 with an $IC_{50}$ of 100 nM or less, preferably 50 nM or less, and more preferably 10 nM or less.

In a further aspect, the present invention provides for a compound selected from (R)-(+)-5-(p-cyanophenyl)-5,6,7,8-tetrahydroimidazo[1,5-a]pyridine and a pharmaceutically acceptable salt thereof, wherein said compound has a specific optical rotation $[\alpha]_D^{20}$ ($CH_3CN:H_2O$ 1:1 (v/v)), $[\alpha]_D^{20}$ (ethanol) or $[\alpha]_D^{25}$ (ethanol), preferably $[\alpha]_D^{20}$ ($CH_3CN:H_2O$ 1:1 (v/v)), of at least +95°, preferably of at least +96°, more preferably of at least +97°, even more preferably of at least +98°, and wherein preferably said compound is (R)-(+)-5-(p-cyanophenyl)-5,6,7,8-tetrahydroimidazolium[1,5-a]pyridine dihydrogen phosphate, and wherein further preferably said compound has a selectivity for aldosterone synthase over aromatase of 50 or more, preferably 100 or more, most preferably 700 or more; wherein said selectivity is determined by the ratio of the $IC_{50}$ values for inhibition of aromatase and aldosterone synthase; wherein the $IC_{50}$ values for inhibition of aromatase and aldosterone synthase are both measured, preferably concomitantly, in the NCI-H295R adrenal cell assay described in Example 8. In a very preferred embodiment, said compound is (R)-(+)-5-(p-cyanophenyl)-5,6,7,8-tetrahydroimidazolium[1,5-a]pyridine dihydrogen phosphate and has a specific optical rotation $[\alpha]_D^{20}$ ($CH_3CN:H_2O$ 1:1 (v/v)) of at least +95°, preferably of at least +96°, more preferably of at least +97°, even more preferably of at least +98°, and wherein preferably said compound has a selectivity for aldosterone synthase over aromatase of 50 or more, preferably 100 or more, most preferably 700 or more; wherein said selectivity is determined by the ratio of the $IC_{50}$ values for inhibition of aromatase and aldosterone synthase; wherein the $IC_{50}$ values for inhibition of aldosterone synthase and aromatase are both measured, preferably concomitantly, in the NCI-H295R adrenal cell assay described in Example 8.

In a further aspect, the present invention provides for a compound selected from (R)-(+)-5-(p-cyanophenyl)-5,6,7,8-tetrahydroimidazo[1,5-a]pyridine and a pharmaceutically acceptable salt thereof, wherein said compound inhibits aromatase activity in the cell-free human recombinant aromatase enzyme assay described in Example 8 with an $IC_{50}$ of 700 nM or more, preferably 1000 nM or more, and more preferably 1500 nM or more; and wherein preferably said compound has an enantiomeric excess of the (R) form higher than or equal to 97%, and wherein further preferably said compound is (R)-(+)-5-(p-cyanophenyl)-5,6,7,8-tetrahydroimidazolium[1,5-a]pyridine dihydrogen phosphate.

In a further aspect, the present invention provides for a compound selected from (R)-(+)-5-(p-cyanophenyl)-5,6,7,8-tetrahydroimidazo[1,5-a]pyridine and a pharmaceutically acceptable salt thereof, wherein said compound inhibits aldosterone synthase in the NCI-H295R adrenal cell assay described in Example 8 with an $IC_{50}$ of 100 nM or less, preferably 50 nM or less, and more preferably 10 nM or less; and wherein preferably said compound has an enantiomeric excess of the (R) form higher than or equal to 97%, and wherein further preferably said compound is (R)-(+)-5-(p-cyanophenyl)-5,6,7,8-tetrahydroimidazolium[1,5-a]pyridine dihydrogen phosphate.

In a further aspect, the present invention provides for a compound selected from (R)-(+)-5-(p-cyanophenyl)-5,6,7,8-tetrahydroimidazo[1,5-a]pyridine and a pharmaceutically acceptable salt thereof, wherein said compound has a selectivity for aldosterone synthase over aromatase of 50 or more, preferably 100 or more, most preferably 700 or more; wherein said selectivity is determined by the ratio of the $IC_{50}$ values for inhibition of aromatase and aldosterone synthase; wherein the $IC_{50}$ values for inhibition of aldosterone synthase and aromatase are both measured, preferably concomitantly, in the NCI-H295R adrenal cell assay described in Example 8; and wherein preferably said compound has an enantiomeric excess of the (R) form higher than or equal to 97%, and wherein further preferably said compound is (R)-(+)-5-(p-cyanophenyl)-5,6,7,8-tetrahydroimidazolium[1,5-a]pyridine dihydrogen phosphate.

DETAILED DESCRIPTION OF THE INVENTION

Figure 1:
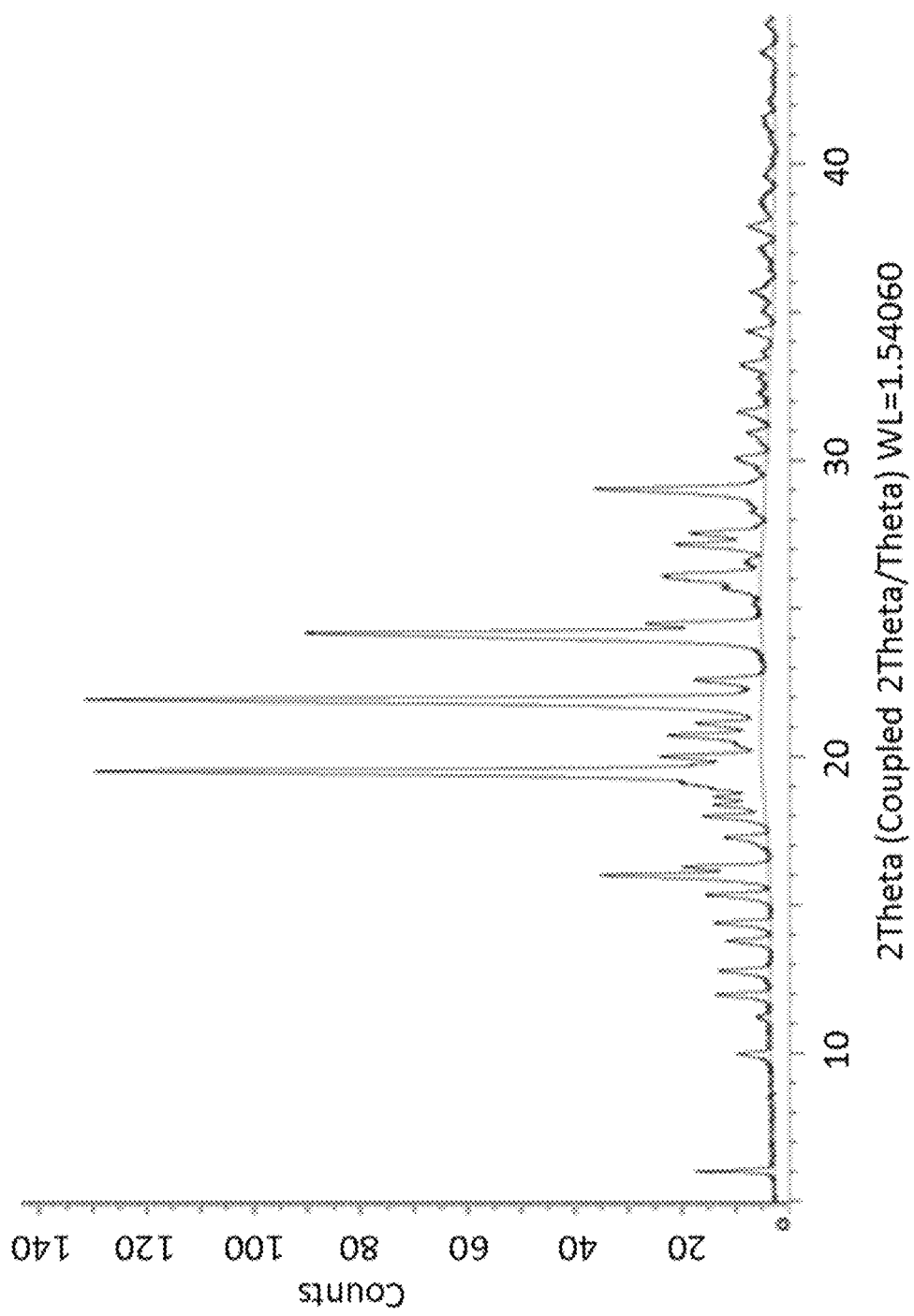
FIG. 1: X-ray powder diffraction (XRPD) diffractogram of (R)-(+)-5-(p-cyanophenyl)-5,6,7,8-tetrahydroimidazolium[1,5-a]pyridine dihydrogen phosphate. The Y-axis of the diffractogram records the intensity in counts per second whereas the X-axis the degrees 2-theta.

Unless defined otherwise, all technical and scientific terms used herein have the same meanings as commonly understood by one of ordinary skill in the art to which this invention belongs.

The term "about" where used means especially 10%, 5% or 3% (referring to the given numeric value, respectively), if not indicated otherwise. In each of the invention embodiments, "about" can be deleted.

The term "chiral purity" as used herein is defined by the enantiomeric excess (ee) as determined by chiral HPLC (see Examples for details) and calculated by the equation:

$$ee=(A_R-A_S)/(A_R+A_S)\times 100\%,$$

wherein $A_R$ is the area of the (R)-(+)-5-(p-cyanophenyl)-5,6,7,8-tetrahydroimidazo[1,5-a]pyridine peak in the HPLC chromatogram of the sample solution and $A_S$ is the area of the (S)-(+)-5-(p-cyanophenyl)-5,6,7,8-tetrahydroimidazo[1,5-a]pyridine peak in the HPLC chromatogram of the sample solution.

The term "pharmaceutically acceptable salt" as used herein refers to a salt that is pharmaceutically acceptable and that possesses the desired pharmacological activity of the parent compound. Such salts include acid addition salts formed with inorganic acids or organic acids known to the skilled person in the art (P. Heinrich Stahl (Editor), Camille G. Wermuth (Editor); Handbook of Pharmaceutical Salts: Properties, Selection, and Use, 2nd Revised Edition, March 2011, Wiley-VCH, ISBN: 978-3-90639-051-2). A particularly preferred pharmaceutically acceptable salt in the present invention is an acid addition salt formed with phosphoric acid, i.e. a dihydrogen phosphate.

The term "phosphate salt" as used in the present application refers to compounds comprising (R)-(+)-5-(p-cyanophenyl)-5,6,7,8-tetrahydroimidazo[1,5-a]pyridine in its protonated form, i.e. the (R)-(+)-5-(p-cyanophenyl)-5,6,7,8-tetrahydroimidazolium[1,5-a]pyridine cation and further comprising anions derived from phosphoric acid, wherein said anions are typically and preferably selected from dihydrogen phosphate $[H_2PO_4]^-$ and hydrogen phosphate $[HPO_4]^{2-}$. Preferably, the term "phosphate salt" as used in the present application refers to the compound of formula (I) dihydrogen phosphate, that is, wherein the compound of formula (I) is protonated once and the counterion is $[H_2PO_4]^-$ (see FIG. 7 for single crystal X-ray structure) and, thus, the stoichiometry of mono-protonated (R)-(+)-5-(p-cyanophenyl)-5,6,7,8-tetrahydroimidazo[1,5-a]pyridine to dihydrogen phosphate is 1:1. The latter compound is referred herein as (R)-(+)-5-(p-cyanophenyl)-5,6,7,8-tetrahydroimidazolium[1,5-a]pyridine dihydrogen phosphate.

The term "aromatase" refers to CYP19, a member of the cytochrome P450 superfamily, and is also known as estrogen synthase.

The term "aldosterone synthase" refers to the steroid hydroxylase cytochrome P450 enzyme CYP11B2.

The term "amorphous" as used herein, means a supercooled liquid or a viscous liquid which looks like a solid but does not have a regularly repeating arrangement of molecules that is maintained over a long range and does not have a melting point but rather softens or flows above its glass transition temperature.

The terms "crystalline" and "crystalline purity" as interchangeably used herein and related to the inventive compounds, refer to a solid having a regularly repeating arrangement of molecules or external face planes. Preferably, the terms "crystalline" and "crystalline purity" when referring to (R)-(+)-5-(p-cyanophenyl)-5,6,7,8-tetrahydroimidazolium [1,5-a]pyridine dihydrogen phosphate comprising (R)-(+)-5-(p-cyanophenyl)-5,6,7,8-tetrahydroimidazolium[1,5-a] pyridine dihydrogen phosphate refers to the crystalline form I, wherein said crystalline form I is present of at least 60% by total weight, preferably of at least 70% by total weight, further preferably of at least 80% by total weight, again further preferably of at least 90% by total weight, and again further preferably of at least 95% by total weight. Further components may be, for example, amorphous (R)-(+)-5-(p-cyanophenyl)-5,6,7,8-tetrahydroimidazolium[1,5-a]pyridine dihydrogen phosphate. Crystalline purity may be determined by means of XRPD as described herein. Thus, in a preferred embodiment said XRPD can be determined using the following device, parameters and measuring conditions: Instrument: Bruker AXS D2 PHASER; Irradiation: CuKα (30 kV, 10 mA); scan range: 5 to 45° (2 theta value), sample rotation 5 rpm, 0.5s/step, 0.010°/step, 3.0 mm detector slit.

The term "crystalline form I" as used herein refers to the (R)-(+)-5-(p-cyanophenyl)-5,6,7,8-tetrahydroimidazolium[1,5-a]pyridine dihydrogen phosphate, wherein said (R)-(+)-5-(p-cyanophenyl)-5,6,7,8-tetrahydroimidazolium[1,5-a]pyridine dihydrogen phosphate has an X-ray powder diffraction pattern comprising the following 2θ values measured using CuKα radiation: 19.504; 21.919 and 24.159, wherein each peak may vary by ±1 or preferably by 0.5, or further preferably by ±0.2 degrees. In a preferred embodiment, "crystalline form I" as used herein refers to the (R)-(+)-5-(p-cyanophenyl)-5,6,7,8-tetrahydroimidazolium[1,5-a]pyridine dihydrogen phosphate, wherein said (R)-(+)-5-(p-cyanophenyl)-5,6,7,8-tetrahydroimidazolium[1,5-a]pyridine dihydrogen phosphate has an X-ray powder diffraction pattern comprising the following 2θ values measured using CuKα radiation, 19.504; 21.919 and 24.159, wherein each peak may vary by ±1 or preferably by ±0.5, or further preferably by ±0.2 degrees. In a further preferred embodiment, "crystalline form I" as used herein refers to the (R)-(+)-5-(p-cyanophenyl)-5,6,7,8-tetrahydroimidazolium[1,5-a]pyridine dihydrogen phosphate, wherein said (R)-(+)-5-(p-cyanophenyl)-5,6,7,8-tetrahydroimidazolium[1,5-a]pyridine dihydrogen phosphate has an X-ray powder diffraction pattern comprising the following 2θ values measured using CuKα radiation, 19.504; 21.919 and 24.159, wherein each peak may vary by ±0.5, or preferably by ±0.2 degrees. In again a further preferred embodiment, the term "crystalline form I" as used herein refers to the (R)-(+)-5-(p-cyanophenyl)-5,6,7,8-tetrahydroimidazolium[1,5-a]pyridine dihydrogen phosphate, wherein said (R)-(+)-5-(p-cyanophenyl)-5,6,7,8-tetrahydroimidazolium[1,5-a]pyridine dihydrogen phosphate has an X-ray powder diffraction pattern comprising the following 2θ values measured using CuKα radiation, 19.504; 21.919 and 24.159, wherein each peak may vary by ±0.2 degrees. In another preferred embodiment, "crystalline form I" as used herein refers to the (R)-(+)-5-(p-cyanophenyl)-5,6,7,8-tetrahydroimidazolium[1,5-a]pyridine dihydrogen phosphate, wherein said (R)-(+)-5-(p-cyanophenyl)-5,6,7,8-tetrahydroimidazolium[1,5-a]pyridine dihydrogen phosphate has an X-ray powder diffraction pattern comprising the following 2θ values measured using CuKα radiation: 19.504; 21.919; 24.159; 16.003; 26.101; 27.168; 27.542 and 29.029, wherein each peak may vary by ±1 or preferably by ±0.5, or further preferably by ±0.2 degrees. In another preferred embodiment, "crystalline form I" as used herein refers to the (R)-(+)-5-(p-cyanophenyl)-5,6,7,8-tetrahydroimidazolium[1,5-a]pyridine dihydrogen phosphate, wherein said (R)-(+)-5-(p-cyanophenyl)-5,6,7,8-tetrahydroimidazolium[1,5-a]pyridine dihydrogen phosphate has an X-ray powder diffraction pattern comprising the following 2θ values measured using CuKα radiation: 19.504; 21.919; 24.159; 16.003; 26.101; 27.168; 27.542 and 29.029, wherein each peak may vary by ±0.5, or preferably by ±0.2 degrees.

The term "anhydrous" as used herein refers to a crystalline form which contains less than 3%, preferably less than 2.5%, more preferably less than 2%, more preferably less than 1.5%, most preferably less than 1% water of hydration.

The term "non-hygroscopic" means the ability by the inventive pharmaceutically acceptable salts of (R)-(+)-5-(p-cyanophenyl)-5,6,7,8-tetrahydroimidazo[1,5-a]pyridine, and in particular of the phosphate salt of (R)-(+)-5-(p-cyanophenyl)-5,6,7,8-tetrahydroimidazo[1,5-a]pyridine, more preferably the (R)-(+)-5-(p-cyanophenyl)-5,6,7,8-tetrahydroimidazolium[1,5-a]pyridine dihydrogen phosphate, when they occur as powders or granules, to withstand exposure to the water vapor of an ambient atmosphere for 24 hours, weeks, months or years as a premise for commercial use without giving rise to adverse phenomena of aggregating, agglomerating, absorbing water, or deliquescing. Typically and preferably, the term "non-hygroscopic" as used herein and referring to the phosphate salt of (R)-(+)-5-(p-cyanophenyl)-5,6,7,8-tetrahydroimidazo[1,5-a]pyridine, and preferably when referring to the (R)-(+)-5-(p-cyanophenyl)-5,6,7,8-tetrahydroimidazolium[1,5-a]pyridine dihydrogen phosphate, means that on storage in the open under normal ambient conditions, typically and preferably at 20-25° C. and a relative humidity of between 20% and 80%, preferably between 30% and 60%, it preserves its consistency as (preferably free-flowing) powder or granules over a period of at least one day, preferably one week, further preferably one month, again further preferably over a period of at least 3 months, and again further preferably for at least 6 months, and again further preferably or at least 1 year or more, in particular, to meet regulatory ICH standards. Further preferably, the term "non-hygroscopic" as used herein and referring to the phosphate salt of (R)-(+)-5-(p-cyanophenyl)-5,6,7,8-tetrahydroimidazo[1,5-a]pyridine, and preferably when referring to the (R)-(+)-5-(p-cyanophenyl)-5,6,7,8-tetrahydroimidazolium[1,5-a]pyridine dihydrogen phosphate, means that on storage in the open under normal ambient conditions, typically and preferably at 20-25° C. and a relative humidity of between 20% and 80%, preferably between 30% and 60%, for a period of 24 hours, typically and preferably as determined in Example 5, it shows a weight increase of less than 5%, preferably of less than 3%, further preferably of less than 2%, again further preferably of less than 1%. Again further preferably, the term "non-hygroscopic" as used herein and referring to the phosphate salt of (R)-(+)-5-(p-cyanophenyl)-5,6,7,8-tetrahydroimidazo[1,5-a]pyridine, and preferably when referring to the (R)-(+)-5-(p-cyanophenyl)-5,6,7,8-tetrahydroimidazolium[1,5-a]pyridine dihydrogen phosphate, means that on storage in the open under normal ambient conditions, typically and preferably at room temperature, most preferably at 20-25° C. and at a relative humidity of between 20% and 80%, preferably between 30% and 60%, for a period of 24 hours, typically and preferably as determined in Example 5, said phosphate salt, preferably said (R)-(+)-5-(p-cyanophenyl)-5,6,7,8-tetrahydroimidazolium[1,5-a]pyridine dihydrogen phosphate shows a water uptake of less than 5% (wt/wt), preferably of less than 3% (wt/wt), further preferably of less than 2% (wt/wt), again further preferably of less than 1% (wt/wt). Alternatively preferred, the term "non-hygroscopic" as used herein and referring to the phosphate salt of (R)-(+)-5-(p-cyanophenyl)-5,6,7,8-tetrahydroimidazo[1,5-a]pyridine, and preferably when referring to the (R)-(+)-5-(p-cyanophenyl)-5,6,7,8-tetrahydroimidazolium[1,5-a]pyridine dihydrogen phosphate, means that on storage in the open under normal ambient conditions, typically and preferably at 25° C. and a relative humidity of between of about 60%, for a period of 24 hours, preferably for a period of one month, further preferably for a period of at least 3 months, and again further preferably for at least 6 months, and again further preferably or at least 1 year, typically and preferably as determined in Example 9, the water content is less than 0.5 w/w %, preferably less than 0.4 w/w %, and further preferably equal or less than 0.3 w/w %.

The term "pharmaceutically acceptable excipient" as used herein includes any physiologically inert additive that is routinely used in pharmaceutical dosage forms. Pharmaceutically acceptable excipients are selected from the group comprising binders, diluents, carriers, lubricants, glidants, coating additives or combinations thereof.

The term "solubility" as used herein refers to simplified descriptive solubilities (e.g. in water) in accordance with the U.S. Pharmacopoeia, Chapter "General Notices", § 5.30 "Description and Solubility" (and as defined below):

| Descriptive Term | Parts of Solvent Required for 1 Part of Solute |
|---|---|
| Very soluble | Less than 1 |
| Freely soluble | From 1 to 10 |
| Soluble | From 10 to 30 |
| Sparingly soluble | From 30 to 100 |
| Slightly soluble | From 100 to 1,000 |
| Very slightly soluble | From 1,000 to 10,000 |
| Practically insoluble, or Insoluble | Greater than or equal to 10,000 |

The term "woman of childbearing potential" as used herein refers to a premenopausal female capable of becoming pregnant.

The term "pediatric patient" as used herein refers to patient in the age category 0-18, preferably 0-16 years and include preterm and term newborn infants (0-27 days), infants and toddlers (28 days to 23 months), children (2-11 years) and adolescents (2 to 16/18 years).

Accordingly, in one embodiment, there is provided a compound selected from (R)-(+)-5-(p-cyanophenyl)-5,6,7,8-tetrahydroimidazo[1,5-a]pyridine of formula (I) and a pharmaceutically acceptable salt thereof, in particular (R)-(+)-5-(p-cyanophenyl)-5,6,7,8-tetrahydroimidazolium[1,5-a]pyridine dihydrogen phosphate, having a solubility in water of more than 50% vol/vol.

The expression "$IC_{50}$" refers to the half maximal inhibitory concentration as commonly known in the art. The $IC_{50}$ for aromatase is determined by the cell-free human recombinant aromatase assay described in Example 8. The $IC_{50}$ for aldosterone synthase is determined by the human NCI-H295R cell assay described in Example 8. When referring to "selectivity for aldosterone synthase over aromatase", the following ratio is meant:

$$\text{selectivity} = \frac{IC50 \text{ for aromatase}}{IC50 \text{ for aldosterone synthase}}$$

wherein both the $IC_{50}$ for aldosterone synthase and the $IC_{50}$ for aromatase are determined, preferably concomitantly, by the human NCI-H295R cell assay described in Example 8.

As outlined above, the phosphate salt of (R)-(+)-5-(p-cyanophenyl)-5,6,7,8-tetrahydroimidazo[1,5-a]pyridine, preferably the (R)-(+)-5-(p-cyanophenyl)-5,6,7,8-tetrahydroimidazolium[1,5-a]pyridine dihydrogen phosphate, inhibits aldosterone production (aldosterone synthase activity) and estradiol production (aromatase activity) by NCI-H295R adrenal cells with $IC_{50}$'s of 8.1 nM and 5760 nM, respectively (Example 8, Tables 10 and 11); thus demonstrating a selectivity of about 700 for aldosterone synthase over aromatase.

As used herein, the term "a disorder" or "a disease" refers to any derangement or abnormality of function; a morbid physical or mental state. See Dorland's Illustrated Medical Dictionary (VSIB. Saunders Co. 27th ed. 1988).

As used herein, the expression "disease or disorder in which aldosterone over-exposure contributes to the deleterious effects of said disease or disorder" preferably refers to a disease and disorder which is due to the abnormal or inappropriate activity/expression of aldosterone synthase and the biological activity or process which is associated with the abnormal or inappropriate expression of aldosterone synthase. Typical examples of diseases or disorders that are due to abnormal or inappropriate activity/expression of aldosterone synthase are primary and secondary hyperaldosteronism, heart failure, chronic renal failure, hypertension, restenosis, obesity, nephropathy, post-myocardial infarction, renal fibrosis, and coronary heart disease.

As used herein, the term "abnormal activity of aldosterone synthase" refers to an activity of aldosterone synthase which differs from the activity of the wild-type or native gene or protein, or which differs from the activity of the gene or protein in a healthy subject. The abnormal activity can be stronger or weaker than the normal activity.

As used herein, the term "inappropriate activity of aldosterone synthase" refers to the activity of aldosterone synthase of the wild-type or native gene or protein or to the activity of the gene or protein in a healthy subject, which is considered as appropriate in a healthy subject, but the same said activity is considered inappropriate for a diseased subject, i.e. said activity is too strong or too weak for a diseased subject.

As used herein, the term "treating" or "treatment" of any disease or disorder refers to ameliorating the disease or disorder (i.e., arresting or reducing the development of the disease or at least one of the clinical symptoms thereof).

As used herein, the term "specific optical rotation" refers to the specific optical rotation of a solution of the respective compound in a solvent, wherein said solvent is typically and preferably ethanol or $CH_3CN:H_2O$ 1:1 (v/v), further preferably $CH_3CN:H_2O$ 1:1 (v/v), and wherein said specific optical rotation is calculated by the formula: $100 \times \alpha/(1 \times c)$, wherein $\alpha$=observed rotation in degrees; 1=cell path length in decimeters; c=concentration in grams per 100 ml, and wherein the measurement is performed at the sodium D line (i.e. 589.3 nm) at room temperature, typically and preferably at either 20° C. or 25° C. The term "specific optical rotation" is abbreviated as $[\alpha]_D^{20}$ or $[\alpha]_D^{25}$. Typically, for $[\alpha]D^{20}$ or $[\alpha]D^{25}$, either the sign of the rotation (+ or −) and its actual value is indicated herein or $[\alpha]_D^{20}$ or $[\alpha]_D^{25}$ is provided by way of its sign of the rotation (+ or −) and its actual value indicated in degrees (°). The complete unit as determined above (deg $dm^{-1}$ $cm^3$ $g^{-1}$) is typically omitted for the sake of clarity.

In a first aspect, the present invention provides for a compound selected from (R)-(+)-5-(p-cyanophenyl)-5,6,7,8-tetrahydroimidazo[1,5-a]pyridine of formula (I) and a pharmaceutically acceptable salt thereof having an enantiomeric excess (ee) of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9%.

In particular, and in a second aspect, the present invention provides for (R)-(+)-5-(p-cyanophenyl)-5,6,7,8-tetrahydroimidazolium[1,5-a]pyridine dihydrogen phosphate, typically and preferably having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9% and which has been surprisingly found to be non-hygroscopic and stable over an extended period of time, in particular with respect to purity, water content and chiral purity. Furthermore and importantly, the phosphate salt of (R)-(+)-5-(p-cyanophenyl)-5,6,7,8-tetrahydroimidazo[1,5-a]pyridine, and in particular (R)-(+)-5-(p-cyanophenyl)-5,6,7,8-tetrahydroimidazolium[1,5-a]pyridine dihydrogen phosphate is crystalline in one stable form, typically and preferably in said crystalline form I.

Figure 2:
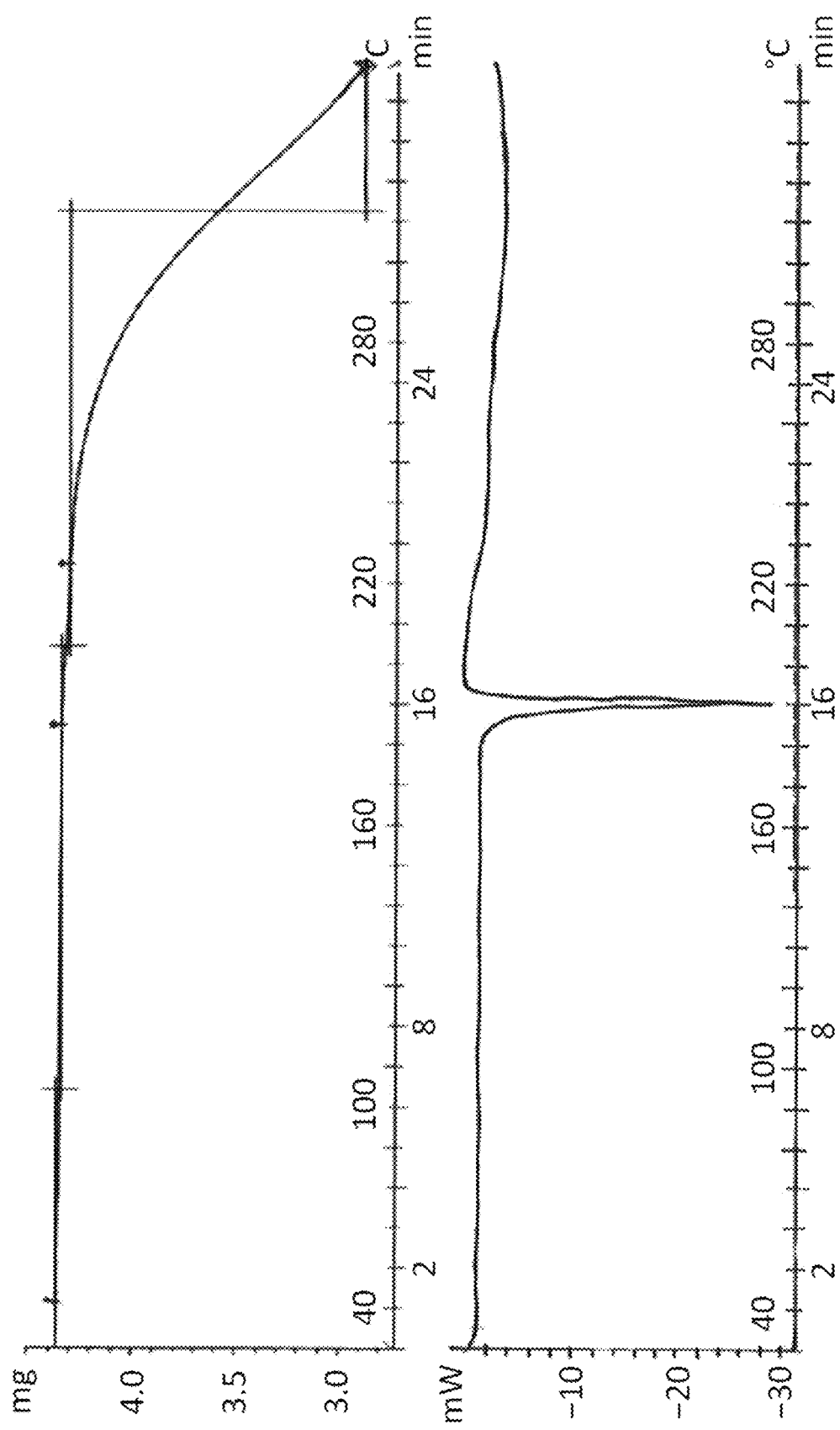
FIG. 2: Thermal gravimetric analysis (TGA)/differential scanning calorimetry (DSC) of (R)-(+)-5-(p-cyanophenyl)-5,6,7,8-tetrahydroimidazolium[1,5-a]pyridine dihydrogen phosphate. The upper panel shows a TGA thermogram of (R)-(+)-5-(p-cyanophenyl)-5,6,7,8-tetrahydroimidazolium [1,5-a]pyridine dihydrogen phosphate. The lower panel shows a DSC thermogram of (R)-(+)-5-(p-cyanophenyl)-5,6,7,8-tetrahydroimidazolium[1,5-a]pyridine dihydrogen phosphate. The thermogram indicates a mass loss of 1.4% up to a temperature of 225° C. (upper panel) which is beyond the melting point of 189° C. (lower panel). The thermogram indicates a melting point with an onset at 188° C. and peaking at 189° C.
Figure 4:
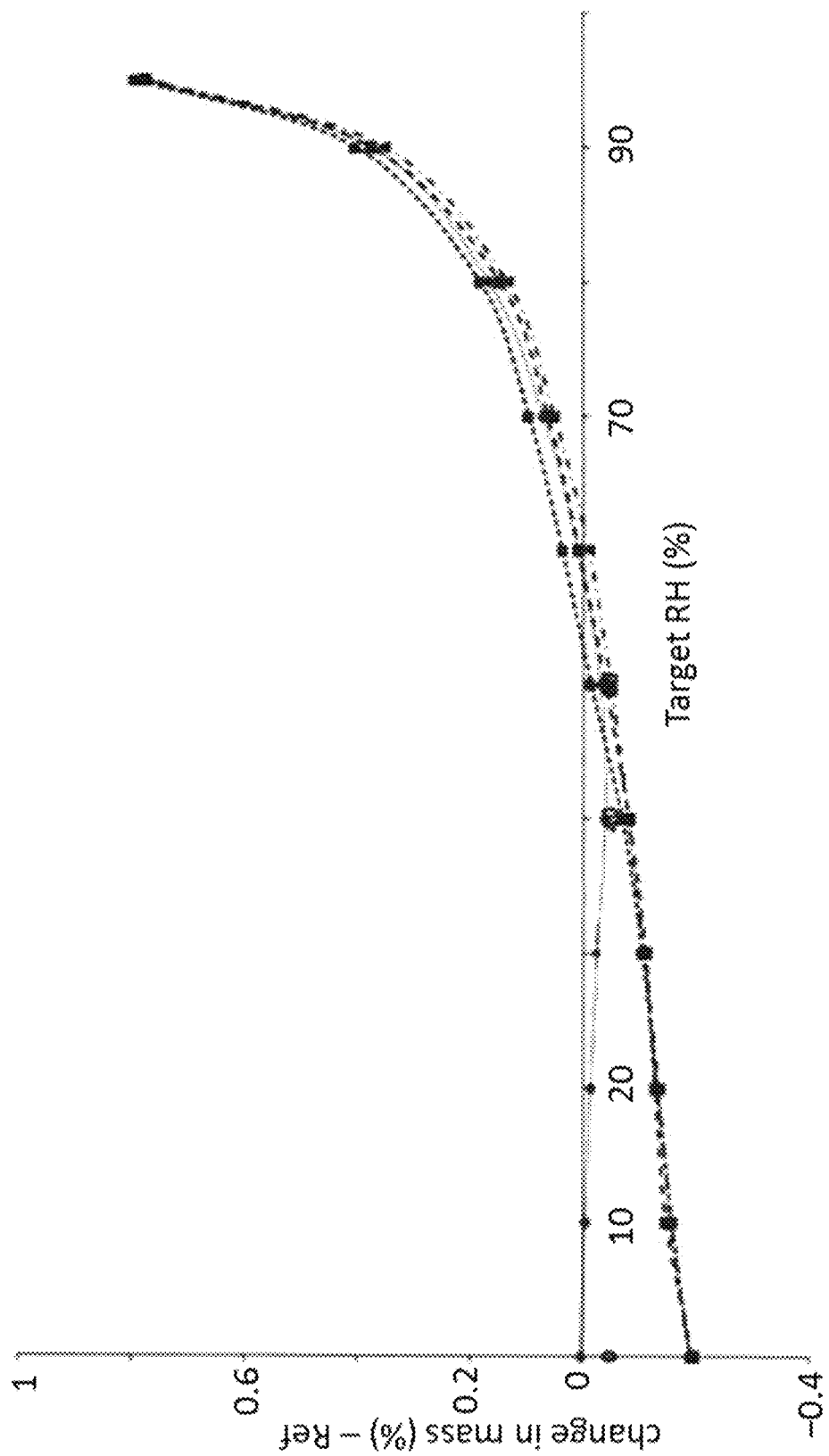
FIG. 4: Dynamic vapor sorption (DVS) isotherm plot of (R)-(+)-5-(p-cyanophenyl)-5,6,7,8-tetrahydroimidazolium [1,5-a]pyridine dihydrogen phosphate (overlay of two sorption/desorption cycles).
The dynamic isotherm plot shows a mass increase, respectively hygroscopicity of up to 1%.
Figure 5:
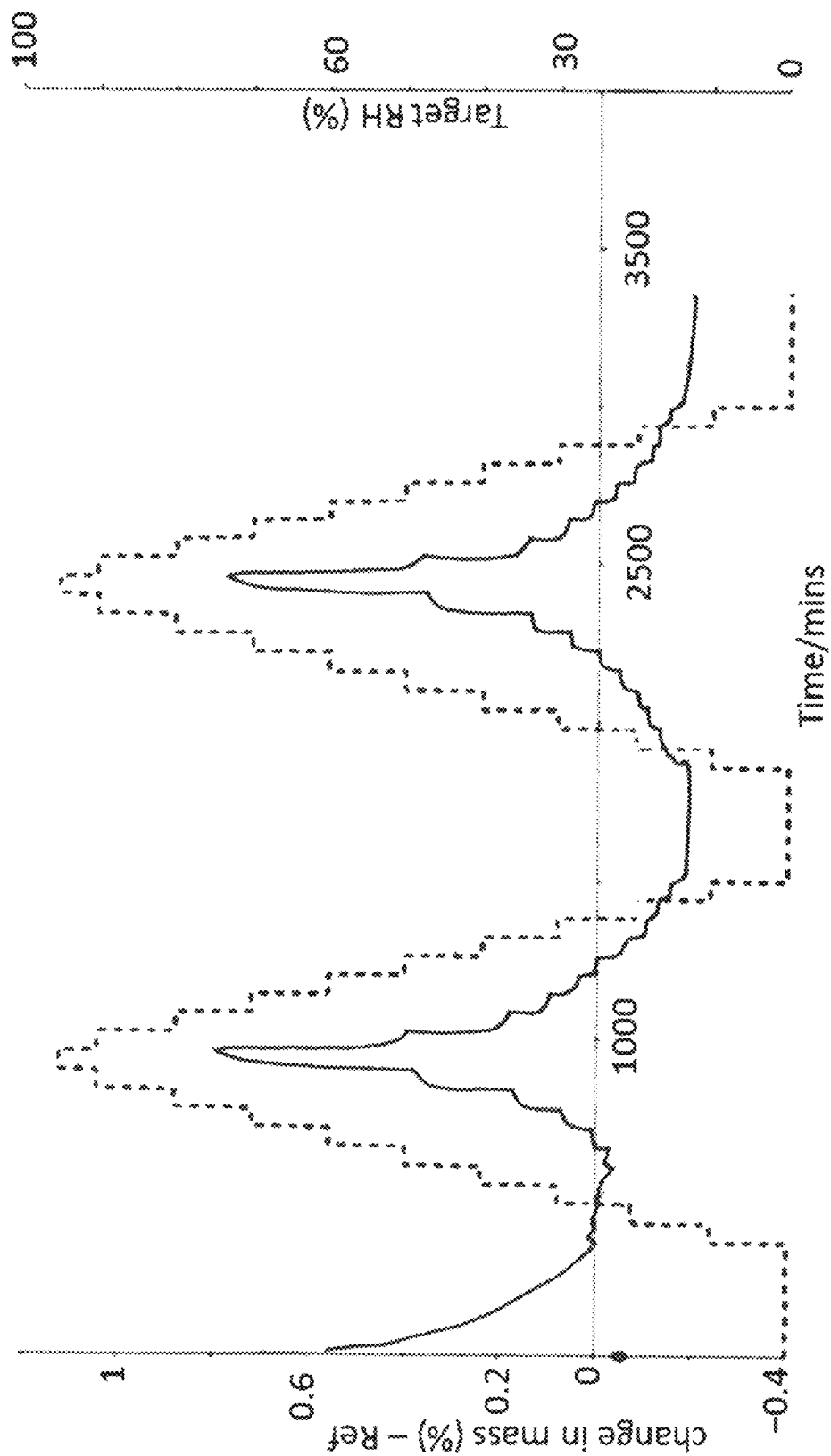
FIG. 5: Dynamic vapor sorption (DVS) mass plot change of (R)-(+)-5-(p-cyanophenyl)-5,6,7,8-tetrahydroimidazolium[1,5-a]pyridine dihydrogen phosphate (dotted curve: relative change in mass; dashed curve: target relative humidity (RH)). The mass plot indicates a reversible water uptake of up to 1%.
Figure 7:
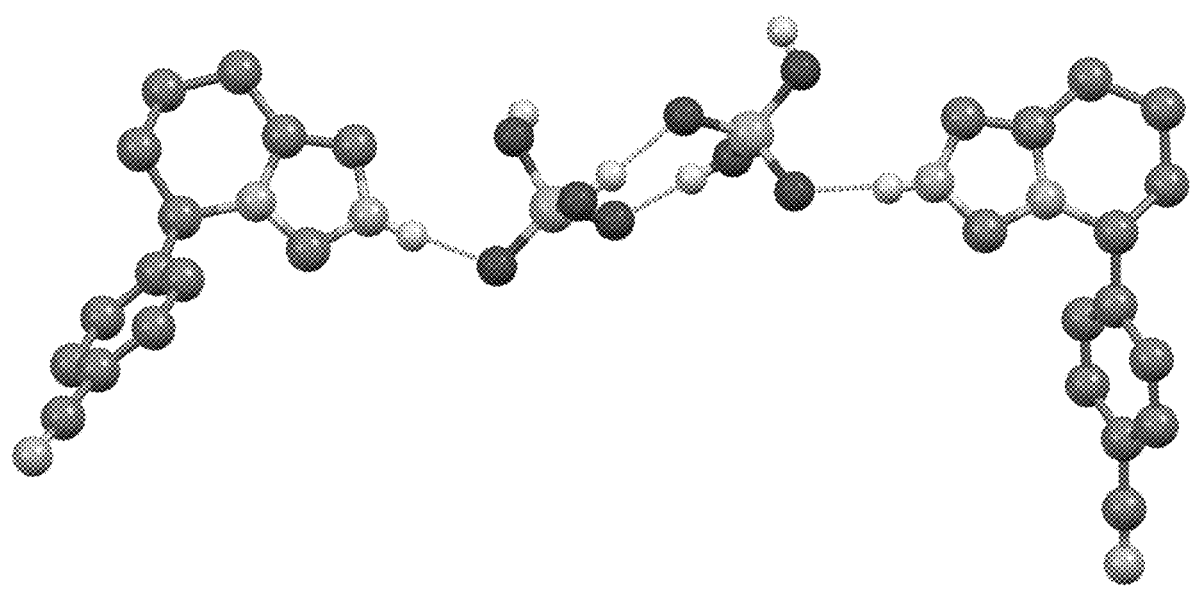
FIG. 7: Crystal structure and absolute configuration of (R)-(+)-5-(p-cyanophenyl)-5,6,7,8-tetrahydroimidazolium [1,5-a]pyridine dihydrogen phosphate determined by single crystal X-ray analysis. The single X-ray determination confirms the R-(+)-configuration on carbon 5.

The water uptake of the inventive (R)-(+)-5-(p-cyanophenyl)-5,6,7,8-tetrahydroimidazolium[1,5-a]pyridine dihydrogen phosphate as measured by Dynamic Vapour Sorption studies is less than 1% at greater than 90% humidity (FIG. 4) and in addition the water uptake is reversible (FIG. 5). Furthermore, the mass loss upon heating up to a temperature of 225° C. was only 1.4% (FIG. 2). In conclusion, the inventive phosphate salt, preferably the (R)-(+)-5-(p-cyanophenyl)-5,6,7,8-tetrahydroimidazolium[1,5-a]pyridine dihydrogen phosphate, is not hygroscopic. As a consequence, the inventive (R)-(+)-5-(p-cyanophenyl)-5,6,7,8-tetrahydroimidazolium[1,5-a]pyridine dihydrogen phosphate can be stored in bulk in customary pharmaceutical containment vessels at ambient conditions. Moreover, the inventive (R)-(+)-5-(p-cyanophenyl)-5,6,7,8-tetrahydroimidazolium[1,5-a]pyridine dihydrogen phosphate has been found to be highly crystalline and having a high level of crystalline purity. Furthermore, and surprisingly the inventive (R)-(+)-5-(p-cyanophenyl)-5,6,7,8-tetrahydroimidazolium[1,5-a]pyridine dihydrogen phosphate with the described exceptional chiral purity is present in one single crystalline form with a defined x-ray structure and R-(+)-absolute configuration on carbon 5, its chiral center (FIG. 1 and Table 1; FIG. 7).

Multiple crystalline forms—so called polymorphs—complicate the manufacturing of pharmaceutical preparations because such forms can interconvert requiring additional provisions to prevent such interconversion. Different polymorphs behave differently in the formulation of pharmaceutical products; they can affect micronization, tablet formation, solubility and also bioavailability. Since even the smallest compound may have hundreds of thousands of possible arrangements of its molecules in a solid crystal, predicting crystal structures and their properties are a great scientific challenge and it is not possible to know a priori whether polymorphism will actually occur for a given molecule. Polymorphism is thus a serious concern when seeking to provide safe and efficacious forms of a drug. Despite this, the inventors have discovered that the crystalline form I of (R)-(+)-5-(p-cyanophenyl)-5,6,7,8-tetrahydroimidazolium[1,5-a]pyridine dihydrogen phosphate is physically stable, i.e. polymorphism was not observed (Example 6, Table 8; Example 7, Table 9 and FIG. 6, Example 9) and can be obtained predictably and reliably (Example 3, step 4). Furthermore, XRPD analysis of (R)-(+)-5-(p-cyanophenyl)-5,6,7,8-tetrahydroimidazolium[1,5-a]pyridine dihydrogen phosphate (FIG. 1 and Table 1) showed that the substance was essentially free of amorphous material (i.e. amorphous material was not detectable). XRPD was performed, if not described otherwise, as described in the Examples section.

Thus, in one embodiment, the present invention provides crystalline (R)-(+)-5-(p-cyanophenyl)-5,6,7,8-tetrahydroimidazolium[1,5-a]pyridine dihydrogen phosphate, preferably anhydrous crystalline (R)-(+)-5-(p-cyanophenyl)-5,6,7,8-tetrahydroimidazolium[1,5-a]pyridine dihydrogen phosphate, more preferably anhydrous crystalline (R)-(+)-5-(p-cyanophenyl)-5,6,7,8-tetrahydroimidazolium[1,5-a]pyridine dihydrogen phosphate having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9%.

The crystals of (R)-(+)-5-(p-cyanophenyl)-5,6,7,8-tetrahydroimidazolium[1,5-a]pyridine dihydrogen phosphate (crystalline form I) are characterized by XRPD (FIG. 1) with the following angles, lattice spacings (d values) and relative line intensities (intensity) of their X-ray powder pattern (Table 1).

TABLE 1

XRPD Peak list of (R)-(+)-5-(p-cyanophenyl)-5,6,7,8-tetrahydroimidazolium[1,5-a]pyridine dihydrogen phosphate crystalline form I

| Index | 2θ Angle | d Value | Relative Intensity |
|---|---|---|---|
| 1 | 6.023129 | 14.6619 | 0.1166064 |
| 2 | 9.969034 | 8.865584 | 0.04637039 |
| 3 | 11.26224 | 7.850313 | 0.01466121 |
| 4 | 11.22848 | 7.873846 | 0.01766241 |
| 5 | 11.96566 | 7.390353 | 0.07938031 |
| 6 | 12.77761 | 6.922504 | 0.07618304 |
| 7 | 13.79347 | 6.414874 | 0.06721209 |
| 8 | 14.39314 | 6.148929 | 0.08399912 |
| 9 | 15.3394 | 5.771677 | 0.09292314 |
| 10 | 16.00317 | 5.533746 | 0.2509092 |
| 11 | 16.27337 | 5.442465 | 0.1271836 |
| 12 | 17.07502 | 5.188714 | 0.01814438 |
| 13 | 17.27593 | 5.128821 | 0.06430446 |
| 14 | 17.9904 | 4.926713 | 0.09392752 |
| 15 | 18.38238 | 4.822532 | 0.07743008 |
| 16 | 18.65471 | 4.752738 | 0.07315308 |
| 17 | 18.96096 | 4.676658 | 0.07685736 |
| 18 | 19.14281 | 4.632641 | 0.1232251 |
| 19 | 19.504 | 4.547657 | 0.9732185 |
| 20 | 20.01265 | 4.433205 | 0.1459729 |
| 21 | 20.58808 | 4.310579 | 0.06427268 |
| 22 | 20.43302 | 4.34294 | 0.03934043 |
| 23 | 20.72112 | 4.283203 | 0.1308791 |
| 24 | 21.12683 | 4.201858 | 0.09223638 |
| 25 | 21.91906 | 4.051746 | 1.00000000 |
| 26 | 22.59202 | 3.932552 | 0.0988786 |
| 27 | 24.44788 | 3.63807 | 0.1554819 |
| 28 | 24.15917 | 3.680887 | 0.6751482 |
| 29 | 24.48119 | 3.633195 | 0.1650803 |
| 30 | 25.70071 | 3.463495 | 0.05630966 |
| 31 | 26.10094 | 3.411286 | 0.1425888 |
| 32 | 26.58127 | 3.350723 | 0.02198978 |
| 33 | 27.16767 | 3.279716 | 0.1315578 |
| 34 | 27.54165 | 3.236025 | 0.09750613 |
| 35 | 27.71408 | 3.216282 | 0.01282637 |
| 36 | 28.27603 | 3.153627 | 0.01739924 |
| 37 | 28.09725 | 3.173285 | 0.004438166 |
| 38 | 28.54909 | 3.124082 | 0.02253263 |
| 39 | 29.02939 | 3.073475 | 0.2474836 |
| 40 | 29.71314 | 3.004288 | 0.01214569 |
| 41 | 30.07578 | 2.968884 | 0.04296284 |
| 42 | 30.68808 | 2.911028 | 0.01120924 |
| 43 | 30.92867 | 2.88893 | 0.02964231 |
| 44 | 31.6379 | 2.825768 | 0.0454447 |
| 45 | 32.27005 | 2.771842 | 0.01273681 |
| 46 | 32.79806 | 2.728414 | 0.01504905 |
| 47 | 33.20638 | 2.695791 | 0.04151051 |
| 48 | 33.23304 | 2.693689 | 0.04147112 |
| 49 | 33.65808 | 2.660638 | 0.009918388 |
| 50 | 34.41793 | 2.603618 | 0.02669827 |
| 51 | 34.35512 | 2.608234 | 0.03452484 |
| 52 | 35.02142 | 2.560122 | 0.01117852 |
| 53 | 35.06671 | 2.556919 | 0.01513675 |
| 54 | 35.68978 | 2.513696 | 0.03497554 |
| 55 | 35.93622 | 2.497021 | 0.01164656 |
| 56 | 36.50305 | 2.459537 | 0.004599076 |
| 57 | 36.56591 | 2.455453 | 0.004500904 |
| 58 | 36.92023 | 2.432697 | 0.01221618 |
| 59 | 37.14021 | 2.418792 | 0.01601023 |
| 60 | 37.89624 | 2.372257 | 0.03661312 |
| 61 | 39.60815 | 2.27358 | 0.01607032 |
| 62 | 40.22464 | 2.240145 | 0.004137916 |

In one embodiment there is provided a crystalline form I of (R)-(+)-5-(p-cyanophenyl)-5,6,7,8-tetrahydroimidazolium[1,5-a]pyridine dihydrogen phosphate, characterized by an X-ray powder diffraction pattern comprising the following 2θ values measured as described in the Examples section: 19.504; 21.919 and 24.159. In one embodiment there is provided a crystalline form I of (R)-(+)-5-(p-cyanophenyl)-5,6,7,8-tetrahydroimidazolium[1,5-a]pyridine dihydrogen phosphate, characterized by an X-ray powder diffraction pattern comprising the following 2θ values measured as described in the Examples section: 19.504; 21.919 and 24.159, wherein each peak may vary by ±1 or preferably by ±0.5, or further preferably by ±0.2 degrees. In a preferred embodiment, said X-ray powder diffraction pattern further comprises the following 2θ values: 16.003; 26.101; 27.168; 27.542 and 29.029. In a preferred embodiment, said X-ray powder diffraction pattern further comprises the following 2θ values: 16.003; 26.101; 27.168; 27.542 and 29.029, wherein each peak may vary by ±1 or preferably by ±0.5, or further preferably by ±0.2 degrees. In a particularly preferred embodiment, there is provided a crystalline form I of (R)-(+)-5-(p-cyanophenyl)-5,6,7,8-tetrahydroimidazolium [1,5-a]pyridine dihydrogen phosphate, characterized by an X-ray powder diffraction pattern comprising at least one, more preferably 2, 3, 4, 5, 6, 7, 8, 9, 10, 11, 12, 13, 14, 15, 16 or all of the following 2θ values: 6.023129; 9.969034; 11.26224; 11.22848; 11.96566; 12.77761; 13.79347; 14.39314; 15.3394; 16.00317; 16.27337; 17.07502; 17.27593; 17.9904; 18.38238; 18.65471; 18.96096; 19.14281; 19.504; 20.01265; 20.58808; 20.43302; 20.72112; 21.12683; 21.91906; 22.59202; 24.44788; 24.15917; 24.48119; 25.70071; 26.10094; 26.58127; 27.16767; 27.54165; 27.71408; 28.27603; 28.09725; 28.54909; 29.02939; 29.71314; 30.07578; 30.68808; 30.92867; 31.6379; 32.27005; 32.79806; 33.20638; 33.23304; 33.65808; 34.41793; 34.35512; 35.02142; 35.06671; 35.68978; 35.93622; 36.50305; 36.56591; 36.92023; 37.14021; 39.60815; 37.89624 and 40.22464. In another particularly preferred embodiment, there is provided a crystalline form I of (R)-(+)-5-(p-cyanophenyl)-5,6,7,8-tetrahydroimidazolium[1,5-a]pyridine dihydrogen phosphate, characterized by an X-ray powder diffraction pattern comprising at least one, more preferably 2, 3, 4, 5, 6, 7, 8, 9, 10, 11, 12, 13, 14, 15, 16 or all of the following 2θ values: 6.023129; 9.969034; 11.26224; 11.22848; 11.96566; 12.77761; 13.79347; 14.39314; 15.3394; 16.00317; 16.27337; 17.07502; 17.27593; 17.9904; 18.38238; 18.65471; 18.96096; 19.14281; 19.504; 20.01265; 20.58808; 20.43302; 20.72112; 21.12683; 21.91906; 22.59202; 24.44788; 24.15917; 24.48119; 25.70071; 26.10094; 26.58127; 27.16767; 27.54165; 27.71408; 28.27603; 28.09725; 28.54909; 29.02939; 29.71314; 30.07578; 30.68808; 30.92867; 31.6379; 32.27005; 32.79806; 33.20638; 33.23304; 33.65808; 34.41793; 34.35512; 35.02142; 35.06671; 35.68978; 35.93622; 36.50305; 36.56591; 36.92023; 37.14021; 39.60815; 37.89624 and 40.22464, wherein each peak may vary by ±1 or preferably by ±0.5, or further preferably by ±0.2 degrees. In another particularly preferred embodiment, there is provided a crystalline form I of (R)-(+)-5-(p-cyanophenyl)-5,6,7,8-tetrahydroimidazolium[1,5-a]pyridine dihydrogen phosphate, characterized by an X-ray powder diffraction pattern comprising at least one, more preferably 2, 3, 4, 5, 6, 7, 8, 9, 10, 11, 12, 13, 14, 15, 16 or all of the following 2θ values: 6.023129; 9.969034; 11.26224; 11.22848; 11.96566; 12.77761; 13.79347; 14.39314; 15.3394; 16.00317; 16.27337; 17.07502; 17.27593; 17.9904; 18.38238; 18.65471; 18.96096; 19.14281; 19.504; 20.01265; 20.58808; 20.43302; 20.72112; 21.12683; 21.91906; 22.59202; 24.44788; 24.15917; 24.48119; 25.70071; 26.10094; 26.58127; 27.16767; 27.54165; 27.71408; 28.27603; 28.09725; 28.54909; 29.02939; 29.71314; 30.07578; 30.68808; 30.92867; 31.6379; 32.27005; 32.79806; 33.20638; 33.23304; 33.65808; 34.41793; 34.35512; 35.02142; 35.06671; 35.68978; 35.93622; 36.50305; 36.56591; 36.92023; 37.14021; 39.60815; 37.89624 and 40.22464, wherein each peak may vary by ±0.5, or preferably by ±0.2 degrees. In one embodiment, the three largest peaks of crystalline form I in the XRPD diffractogram have a relative intensity of 1 to 0.85 to 0.55, especially of 1 to 0.9 to 0.6, more especially of 1 to 0.95 to 0.65, e.g. of 1 to 0.97 to 0.68 (obtainable by integration of each of the peaks in the XRPD diagrams). In a particular embodiment the largest peak is at a 2-theta (θ) value of about 21.919 and the second-largest peak is at a 2-theta (θ) value of about 19.504 and the third-largest peak is at a 2-theta (θ) value of about 24.159, respectively. In a further particular embodiment the largest peak is at a 2-theta (θ) value of about 21.919±0.5, or preferably by ±0.2 degrees, and the second-largest peak is at a 2-theta (θ) value of about 19.504±0.5, or preferably by ±0.2 degrees and the third-largest peak is at a 2-theta (θ) value of about 24.159±0.5, or preferably by ±0.2 degrees, respectively. Preferred is the (R)-(+)-5-(p-cyanophenyl)-5,6,7,8-tetrahydroimidazolium[1,5-a]pyridine dihydrogen phosphate showing an XRPD diffractogram as shown in FIG. 1.

It was further surprisingly found that (R)-(+)-5-(p-cyanophenyl)-5,6,7,8-tetrahydroimidazolium[1,5-a]pyridine dihydrogen phosphate (crystalline form I) has a single sharp and high melting point of 189° C. as measured by DSC (FIG. 2), again indicating high physical stability and which is further very beneficial with regards to drug manufacture, storage and processing to pharmaceutical formulations. Accordingly, in one embodiment, there is provided (R)-(+)-5-(p-cyanophenyl)-5,6,7,8-tetrahydroimidazolium[1,5-a]pyridine dihydrogen phosphate having a melting point of equal or between 184° C. to 193° C., and wherein preferably said (R)-(+)-5-(p-cyanophenyl)-5,6,7,8-tetrahydroimidazolium [1,5-a]pyridine dihydrogen phosphate has a melting point of equal or between 188° C. to 190° C., typically and preferably using thermogravimetry analysis/differential scanning calorimetry (TGA/DSC). In a further embodiment, there is provided (R)-(+)-5-(p-cyanophenyl)-5,6,7,8-tetrahydroimidazolium[1,5-a]pyridine dihydrogen phosphate having a melting point of 184° C., 185° C., 186° C., 187° C., 188° C., 189° C., 190° C., 191° C., 192° C., 193° C. or 194° C., most preferably 189° C. In a further embodiment, there is provided (R)-(+)-5-(p-cyanophenyl)-5,6,7,8-tetrahydroimidazolium[1,5-a]pyridine dihydrogen phosphate having a melting point of 189±5° C., 189±2° C., 189±1° C. or 189±0.5° C. The melting temperatures herein, if not described otherwise, are obtained by TGA/DSC as described in the Examples section.

In addition, the inventors have found that the solubility of (R)-(+)-5-(p-cyanophenyl)-5,6,7,8-tetrahydroimidazolium [1,5-a]pyridine dihydrogen phosphate (crystalline form I) is low in a number of non-aqueous solvents (Example 6, Table 7) which are thus anti-solvents for the salt, thus making it possible to achieve good precipitation and thus good yields and good purity. On the other hand, crystalline form I is very soluble in water (Example 6, Table 8), which is advantageous for providing oral or parenteral formulations.

The (R)-(+)-5-(p-cyanophenyl)-5,6,7,8-tetrahydroimidazolium[1,5-a]pyridine dihydrogen phosphate prepared from the enantiomerically pure (R)-(+)-5-(p-cyanophenyl)-5,6,7,8-tetrahydroimidazo[1,5-a]pyridine free base described herein and thus having an ee of >99.9%, was found to have a specific optical rotation ($[\alpha]_D^{20}$) of +98.1° (CH$_3$CN:H$_2$O 1:1 (v/v); Example 3).

Accordingly, in one very preferred embodiment and aspect of the present invention, there is provided (R)-(+)-5-(p-cyanophenyl)-5,6,7,8-tetrahydroimidazolium[1,5-a]pyridine dihydrogen phosphate having a specific optical rotation ($[\alpha]_D^{20}$) (CH$_3$CN:H$_2$O 1:1 (v/v)) of at least +94°, preferably of at least +95°, further preferably of at least +96°, more preferably of at least +97°, even more preferably of at least +98°.

In a further embodiment, the present invention provides for (R)-(+)-5-(p-cyanophenyl)-5,6,7,8-tetrahydroimidazo[1,5-a]pyridine having a specific optical rotation $[\alpha]_D^2$ (ethanol) of at least +120°, preferably of at least +121°, further preferably of at least +122°, again further preferably of at least +123°, again further preferably of at least +124°, again further preferably of at least +125°, again further preferably of at least +126°, and again further preferably of at least +127°. In another embodiment, the present invention provides for (R)-(+)-5-(p-cyanophenyl)-5,6,7,8-tetrahydroimidazolium[1,5-a]pyridine chloride having a specific optical rotation $[\alpha]_D^{20}$ (ethanol) of at least +95°, preferably of at least +96°, further preferably of at least +97°, more preferably of at least +98°, even more preferably of at least +99°, further preferably of at least +100°, more preferably of at least +101, even more preferably of at least +102°, and again more preferably of at least +103°, even more preferably of at least +104°.

In a very preferred aspect, the present invention provides (R)-(+)-5-(p-cyanophenyl)-5,6,7,8-tetrahydroimidazolium[1,5-a]pyridine dihydrogen phosphate, preferably crystalline (R)-(+)-5-(p-cyanophenyl)-5,6,7,8-tetrahydroimidazolium[1,5-a]pyridine dihydrogen phosphate, more preferably anhydrous crystalline (R)-(+)-5-(p-cyanophenyl)-5,6,7,8-tetrahydroimidazolium[1,5-a]pyridine dihydrogen phosphate.

In again a very preferred embodiment and aspect, the present invention provides (R)-(+)-5-(p-cyanophenyl)-5,6,7,8-tetrahydroimidazolium[1,5-a]pyridine dihydrogen phosphate, preferably crystalline (R)-(+)-5-(p-cyanophenyl)-5,6,7,8-tetrahydroimidazolium[1,5-a]pyridine dihydrogen phosphate, more preferably anhydrous crystalline (R)-(+)-5-(p-cyanophenyl)-5,6,7,8-tetrahydroimidazolium[1,5-a]pyridine dihydrogen phosphate, having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9%.

In again a very preferred embodiment and aspect, the present invention provides crystalline (R)-(+)-5-(p-cyanophenyl)-5,6,7,8-tetrahydroimidazolium[1,5-a]pyridine dihydrogen phosphate, preferably anhydrous crystalline (R)-(+)-5-(p-cyanophenyl)-5,6,7,8-tetrahydroimidazolium[1,5-a]pyridine dihydrogen phosphate, having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9%, and wherein preferably said (R)-(+)-5-(p-cyanophenyl)-5,6,7,8-tetrahydroimidazolium[1,5-a]pyridine dihydrogen phosphate is a crystalline form I of (R)-(+)-5-(p-cyanophenyl)-5,6,7,8-tetrahydroimidazolium[1,5-a]pyridine dihydrogen phosphate, wherein said crystalline form I has an X-ray powder diffraction pattern comprising the following 2θ values measured using CuKα radiation: 19.504; 21.919 and 24.159, wherein each peak may vary by ±0.5, or preferably by ±0.2 degrees.

In again a very preferred embodiment and aspect, the present invention provides crystalline (R)-(+)-5-(p-cyanophenyl)-5,6,7,8-tetrahydroimidazolium[1,5-a]pyridine dihydrogen phosphate, preferably anhydrous crystalline (R)-(+)-5-(p-cyanophenyl)-5,6,7,8-tetrahydroimidazolium[1,5-a]pyridine dihydrogen phosphate, having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9%, and wherein said (R)-(+)-5-(p-cyanophenyl)-5,6,7,8-tetrahydroimidazolium[1,5-a]pyridine dihydrogen phosphate is a crystalline form I of (R)-(+)-5-(p-cyanophenyl)-5,6,7,8-tetrahydroimidazolium[1,5-a]pyridine dihydrogen phosphate, wherein said crystalline form I has an X-ray powder diffraction pattern comprising the following 2θ values measured using CuKα radiation: 19.504; 21.919 and 24.159, wherein each peak may vary by ±0.5, or preferably by ±0.2 degrees, wherein preferably said XRPD can be determined using the following device, parameters and measuring conditions: Instrument: Bruker AXS D2 PHASER; Irradiation: CuKα (30 kV, 10 mA); scan range: 5 to 45° (2 theta value), sample rotation 5 rpm, 0.5s/step, 0.010°/step, 3.0 mm detector slit.

In again a very preferred embodiment and aspect, the present invention provides crystalline (R)-(+)-5-(p-cyanophenyl)-5,6,7,8-tetrahydroimidazolium[1,5-a]pyridine dihydrogen phosphate, preferably anhydrous crystalline (R)-(+)-5-(p-cyanophenyl)-5,6,7,8-tetrahydroimidazolium[1,5-a]pyridine dihydrogen phosphate, having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9%, and wherein said (R)-(+)-5-(p-cyanophenyl)-5,6,7,8-tetrahydroimidazolium[1,5-a]pyridine dihydrogen phosphate is a crystalline form I of (R)-(+)-5-(p-cyanophenyl)-5,6,7,8-tetrahydroimidazolium[1,5-a]pyridine dihydrogen phosphate, wherein said crystalline form I has an X-ray powder diffraction pattern comprising the following 2θ values measured using CuKα radiation: 19.504; 21.919 and 24.159, wherein each peak may vary by ±0.5, or preferably by ±0.2 degrees, said XRPD can be determined using the following device, parameters and measuring conditions: Instrument: Bruker AXS D2 PHASER; Irradiation: CuKα (30 kV, 10 mA); scan range: 5 to 45° (2 theta value), sample rotation 5 rpm, 0.5s/step, 0.010°/step, 3.0 mm detector slit.

(R)-(+)-5-(p-cyanophenyl)-5,6,7,8-tetrahydroimidazolium[1,5-a]pyridine dihydrogen phosphate has further been found to be anhydrous (Example 3 and 5). Thus, in one embodiment, the present invention provides for anhydrous (R)-(+)-5-(p-cyanophenyl)-5,6,7,8-tetrahydroimidazolium[1,5-a]pyridine dihydrogen phosphate. In a particularly preferred embodiment, the present invention provides for anhydrous (R)-(+)-5-(p-cyanophenyl)-5,6,7,8-tetrahydroimidazolium[1,5-a]pyridine dihydrogen phosphate having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9%.

In a further particularly preferred embodiment, the present invention provides for anhydrous (R)-(+)-5-(p-cyanophenyl)-5,6,7,8-tetrahydroimidazolium[1,5-a]pyridine dihydrogen phosphate crystalline form I.

In yet a further particularly preferred embodiment, the present invention provides for anhydrous (R)-(+)-5-(p-cyanophenyl)-5,6,7,8-tetrahydroimidazolium[1,5-a]pyridine dihydrogen phosphate crystalline form I as defined herein, having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9%.

As outlined above, the inventors have surprisingly found that (R)-(+)-5-(p-cyanophenyl)-5,6,7,8-tetrahydroimidazo[1,5-a]pyridine prepared by the process of the invention (Example 3), as well as its phosphate salt, preferably the (R)-(+)-5-(p-cyanophenyl)-5,6,7,8-tetrahydroimidazolium[1,5-a]pyridine dihydrogen phosphate, exhibit an unprecedented low inhibitory activity for aromatase (Example 8), which is crucial to avoid side effects related to inhibition of aromatase when using the compounds of the invention in methods of treating diseases or disorders related to enhanced aldosterone synthase activity and/or enhanced levels of aldosterone, in particular when used for women of child bearing potential and pediatric patients. Accordingly, in a further aspect, the present invention provides for a compound selected from (R)-(+)-5-(p-cyanophenyl)-5,6,7,8-tetrahydroimidazo[1,5-a]pyridine and a pharmaceutically acceptable salt thereof, in particular the phosphate salt thereof, further preferably the (R)-(+)-5-(p-cyanophenyl)-5,6,7,8-tetrahydroimidazolium[1,5-a]pyridine dihydrogen phosphate, wherein said compound inhibits aromatase activity in the cell-free human recombinant aromatase enzyme assay described in Example 8 with an $IC_{50}$ of 700 nM or more, preferably 750 nM or more, more preferably 800 nM or more, more preferably 850 nM or more, more preferably 900 nM or more, more preferably 950 nM or more, more preferably 1000 nM or more, more preferably 1050 nM or more, more preferably 1100 nM or more, more preferably 1150 nM or more, more preferably 1200 nM or more, more preferably 1250 nM or more, more preferably 1300 nM or more, more preferably 1350 nM or more, more preferably 1400 nM or more, more preferably 1450 nM or more, more preferably 1500 nM or more, more preferably 1550 nM or more, most preferably at least 1600 nM, e.g. 1610 nM or 1620 nM or 1630 nM or 1640 nM or at least 1650 nM.

In yet a further aspect, the present invention provides for a compound selected from (R)-(+)-5-(p-cyanophenyl)-5,6,7,8-tetrahydroimidazo[1,5-a]pyridine and a pharmaceutically acceptable salt thereof, in particular the phosphate salt thereof, further preferably the (R)-(+)-5-(p-cyanophenyl)-5,6,7,8-tetrahydroimidazolium[1,5-a]pyridine dihydrogen phosphate, wherein said compound inhibits aldosterone synthase in the NCI-H295R adrenal cell assay described in Example 8 with an $IC_{50}$ of 100 nM or less. In one embodiment, the compounds of the invention inhibit aldosterone synthase in the NCI-H295R adrenal cell assay described in Example 8 with an $IC_{50}$ of 90 nM or less, 80 nM or less, 70 nM or less, 60 nM or less, 50 nM or less, 40 nM or less, 35 nM or less, 30 nM or less, 25 nM or less, or 20 nM or less; in particular 15 nM or less, e.g., 15 nM, 14 nM, 13 nM, 12 nM, 11 nM, 10 nM, 9 nM, 8 nM, 7 nM, 6 nM, 5 nM, 4 nM, 3 nM, 2 nM or 1 nM or less. In a preferred embodiment, the compounds of the invention inhibit aldosterone synthase in the NCI-H295R adrenal cell assay described in Example 8 with an $IC_{50}$ of 10 nM or less.

In yet a further aspect, the present invention provides for a compound selected from (R)-(+)-5-(p-cyanophenyl)-5,6,7,8-tetrahydroimidazo[1,5-a]pyridine and a pharmaceutically acceptable salt thereof, wherein said compound has a selectivity for aldosterone synthase over aromatase of 30 or more, preferably 50 or more, more preferably 100 or more, more preferably 150 or more, more preferably 200 or more, more preferably 250 or more, more preferably 300 or more, more preferably 350 or more, more preferably 400 or more, more preferably 450 or more, more preferably 500 or more, more preferably 550 or more, more preferably 600 or more, more preferably 650 or more, most preferably 700 or more, wherein said selectivity is determined by the ratio of the $IC_{50}$ values for inhibition of aromatase and aldosterone synthase; and wherein the $IC_{50}$ values for inhibition of aldosterone synthase and aromatase are both measured, preferably concomitantly, in the NCI-H295R adrenal cell assay described in Example 8.

Thus, in again a very preferred embodiment and aspect, the present invention provides crystalline (R)-(+)-5-(p-cyanophenyl)-5,6,7,8-tetrahydroimidazolium[1,5-a]pyridine dihydrogen phosphate, preferably anhydrous crystalline (R)-(+)-5-(p-cyanophenyl)-5,6,7,8-tetrahydroimidazolium[1,5-a]pyridine dihydrogen phosphate, having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9%, wherein said (R)-(+)-5-(p-cyanophenyl)-5,6,7,8-tetrahydroimidazolium[1,5-a]pyridine dihydrogen phosphate is a crystalline form I of (R)-(+)-5-(p-cyanophenyl)-5,6,7,8-tetrahydroimidazolium[1,5-a]pyridine dihydrogen phosphate, wherein said crystalline form I has an X-ray powder diffraction pattern comprising the following 2θ values measured using CuKα radiation: 19.504; 21.919 and 24.159, wherein each peak may vary by ±0.5, or preferably by ±0.2 degrees, said XRPD can typically and preferably be determined using the following device, parameters and measuring conditions: Instrument: Bruker AXS D2 PHASER; Irradiation: CuKα (30 kV, 10 mA); scan range: 5 to 45° (2 theta value), sample rotation 5 rpm, 0.5s/step, 0.010°/step, 3.0 mm detector slit, and wherein said (R)-(+)-5-(p-cyanophenyl)-5,6,7,8-tetrahydroimidazolium[1,5-a]pyridine dihydrogen phosphate inhibits aromatase activity in the cell-free human recombinant aromatase enzyme assay described in Example 8 with an $IC_{50}$ of 700 nM or more, preferably 750 nM or more, more preferably 800 nM or more, more preferably 850 nM or more, more preferably 900 nM or more, more preferably 950 nM or more, more preferably 1000 nM or more, more preferably 1050 nM or more, more preferably 1100 nM or more, more preferably 1150 nM or more, more preferably 1200 nM or more, more preferably 1250 nM or more, more preferably 1300 nM or more, more preferably 1350 nM or more, more preferably 1400 nM or more, more preferably 1450 nM or more, more preferably 1500 nM or more, more preferably 1550 nM or more, most preferably at least 1600 nM, e.g. 1610 nM or 1620 nM or 1630 nM or 1640 nM or at least 1650 nM.

In again a very preferred embodiment and aspect, the present invention provides crystalline (R)-(+)-5-(p-cyanophenyl)-5,6,7,8-tetrahydroimidazolium[1,5-a]pyridine dihydrogen phosphate, preferably anhydrous crystalline (R)-(+)-5-(p-cyanophenyl)-5,6,7,8-tetrahydroimidazolium[1,5-a]pyridine dihydrogen phosphate, having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9%, wherein said (R)-(+)-5-(p-cyanophenyl)-5,6,7,8-tetrahydroimidazolium[1,5-a]pyridine dihydrogen phosphate is a crystalline form I of (R)-(+)-5-(p-cyanophenyl)-5,6,7,8-tetrahydroimidazolium[1,5-a]pyridine dihydrogen phosphate, wherein said crystalline form I has an X-ray powder diffraction pattern comprising the following 2θ values measured using CuKα radiation: 19.504; 21.919 and 24.159, wherein each peak may vary by ±0.5, or preferably by ±0.2 degrees, said XRPD can typically and preferably be determined using the following device, parameters and measuring conditions: Instrument: Bruker AXS D2 PHASER; Irradiation: CuKα (30 kV, 10 mA); scan range: 5 to 45° (2 theta value), sample rotation 5 rpm, 0.5s/step, 0.010°/step, 3.0 mm detector slit, and wherein said (R)-(+)-5-(p-cyanophenyl)-5,6,7,8-tetrahydroimidazolium[1,5-a]pyridine dihydrogen phosphate inhibits aldosterone synthase in the NCI-H295R adrenal cell assay described in Example 8 with an $IC_{50}$ of 90 nM or less, 80 nM or less, 70 nM or less, 60 nM or less, 50 nM or less, 40 nM or less, 35 nM or less, 30 nM or less, 25 nM or less, or 20 nM or less; in particular 15 nM or less, e.g., 15 nM, 14 nM, 13 nM, 12 nM, 11 nM, 10 nM, 9 nM, 8 nM, 7 nM, 6 nM, 5 nM, 4 nM, 3 nM, 2 nM or 1 nM or less. In a preferred embodiment, the compounds of the invention inhibit aldosterone synthase in the NCI-H295R adrenal cell assay described in Example 8 with an $IC_{50}$ of 10 nM or less.

In again a very preferred embodiment and aspect, the present invention provides crystalline (R)-(+)-5-(p-cyanophenyl)-5,6,7,8-tetrahydroimidazolium[1,5-a]pyridine dihydrogen phosphate, preferably anhydrous crystalline (R)-(+)-5-(p-cyanophenyl)-5,6,7,8-tetrahydroimidazolium[1,5-a]pyridine dihydrogen phosphate, having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9%, wherein said (R)-(+)-5-(p-cyanophenyl)-5,6,7,8-tetrahydroimidazolium[1,5-a]pyridine dihydrogen phosphate is a crystalline form I of (R)-(+)-5-(p-cyanophenyl)-5,6,7,8-tetrahydroimidazolium[1,5-a]pyridine dihydrogen phosphate, wherein said crystalline form I has an X-ray powder diffraction pattern comprising the following 2θ values measured using CuKα radiation: 19.504; 21.919 and 24.159, wherein each peak may vary by ±0.5, or preferably by ±0.2 degrees, said XRPD can typically and preferably be determined using the following device, parameters and measuring conditions: Instrument: Bruker AXS D2 PHASER; Irradiation: CuKα (30 kV, 10 mA); scan range: 5 to 45° (2 theta value), sample rotation 5 rpm, 0.5s/step, 0.010/step, 3.0 mm detector slit, and wherein said (R)-(+)-5-(p-cyanophenyl)-5,6,7,8-tetrahydroimidazolium[1,5-a]pyridine dihydrogen phosphate has a selectivity for aldosterone synthase over aromatase of 30 or more, preferably 50 or more, more preferably 100 or more, more preferably 150 or more, more preferably 200 or more, more preferably 250 or more, more preferably 300 or more, more preferably 350 or more, more preferably 400 or more, more preferably 450 or more, more preferably 500 or more, more preferably 550 or more, more preferably 600 or more, more preferably 650 or more, most preferably 700 or more, wherein said selectivity is determined by the ratio of the $IC_{50}$ values for inhibition of aromatase and aldosterone synthase; and wherein the $IC_{50}$ values for inhibition of aldosterone synthase and aromatase are both measured, preferably concomitantly, in the NCI-H295R adrenal cell assay described in Example 8.

In one aspect, the present invention provides for (R)-(+)-5-(p-cyanophenyl)-5,6,7,8-tetrahydroimidazo[1,5-a]pyridine having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9% for use as a medicament.

In a further aspect, the present invention provides for (R)-(+)-5-(p-cyanophenyl)-5,6,7,8-tetrahydroimidazolium [1,5-a]pyridine dihydrogen phosphate for use as a medicament, wherein preferably said dihydrogen phosphate has an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9%.

The present invention further provides for (R)-(+)-5-(p-cyanophenyl)-5,6,7,8-tetrahydroimidazo[1,5-a]pyridine as well as the phosphate salt thereof, preferably the (R)-(+)-5-(p-cyanophenyl)-5,6,7,8-tetrahydroimidazolium[1,5-a]pyridine dihydrogen phosphate, typically and preferably having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9% for use in a method of the treatment of a disease or disorder in humans including women of child bearing potential and pediatric patients, in which aldosterone over-exposure contributes to the deleterious effects of said disease or disorder, typically and preferably, wherein said disease or disorder is selected from primary and secondary hyperaldosteronism, heart failure, chronic renal failure, hypertension, restenosis, obesity, nephropathy, post-myocardial infarction, renal fibrosis, and coronary heart disease.

Further, the present invention provides for (R)-(+)-5-(p-cyanophenyl)-5,6,7,8-tetrahydroimidazo[1,5-a]pyridine as well as the phosphate salt thereof, preferably the (R)-(+)-5-(p-cyanophenyl)-5,6,7,8-tetrahydroimidazolium[1,5-a]pyridine dihydrogen phosphate, typically and preferably having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9% for use in a method of the treatment of a disease or disorder, wherein said disease or disorder is selected from primary and secondary hyperaldosteronism, heart failure, chronic renal failure, hypertension, restenosis, obesity, nephropathy, post-myocardial infarction, renal fibrosis, and coronary heart disease. Further preferably, said method is in particular suited for use in humans including preferably for women of child bearing potential and pediatric patients.

In a further very preferred embodiment and aspect, the present invention provides for provides crystalline (R)-(+)-5-(p-cyanophenyl)-5,6,7,8-tetrahydroimidazolium[1,5-a]pyridine dihydrogen phosphate, preferably anhydrous crystalline (R)-(+)-5-(p-cyanophenyl)-5,6,7,8-tetrahydroimidazolium[1,5-a]pyridine dihydrogen phosphate, having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9%, for use in a method of treating a disease or disorder in a human, wherein said disease or disorder is selected from primary and secondary hyperaldosteronism, heart failure, chronic renal failure, hypertension, restenosis, obesity, nephropathy, post-myocardial infarction, renal fibrosis, and coronary heart disease, wherein preferably said human is a woman of child bearing potential or a pediatric patient.

In a further very preferred embodiment and aspect, the present invention provides for provides crystalline (R)-(+)-5-(p-cyanophenyl)-5,6,7,8-tetrahydroimidazolium[1,5-a]pyridine dihydrogen phosphate, preferably anhydrous crystalline (R)-(+)-5-(p-cyanophenyl)-5,6,7,8-tetrahydroimidazolium[1,5-a]pyridine dihydrogen phosphate, having an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9%, for use in a method of treating a disease or disorder in a human, wherein said disease or disorder is selected from primary and secondary hyperaldosteronism, heart failure, chronic renal failure, hypertension, restenosis, obesity, nephropathy, post-myocardial infarction, renal fibrosis, and coronary heart disease, wherein preferably said human is a woman of child bearing potential or a pediatric patient, and wherein said (R)-(+)-5-(p-cyanophenyl)-5,6,7,8-tetrahydroimidazolium[1,5-a]pyridine dihydrogen phosphate inhibits aromatase activity in the cell-free human recombinant aromatase enzyme assay described in Example 8 with an $IC_{50}$ of 700 nM or more, preferably 750 nM or more, more preferably 800 nM or more, more preferably 850 nM or more, more preferably 900 nM or more, more preferably 950 nM or more, more preferably 1000 nM or more, more preferably 1050 nM or more, more preferably 1100 nM or more, more preferably 1150 nM or more, more preferably 1200 nM or more, more preferably 1250 nM or more, more preferably 1300 nM or more, more preferably 1350 nM or more, more preferably 1400 nM or more, more preferably 1450 nM or more, more preferably 1500 nM or more, more preferably 1550 nM or more, most preferably at least 1600 nM, e.g. 1610 nM or 1620 nM or 1630 nM or 1640 nM or at least 1650 nM.

In a further aspect, the present invention provides for a process for preparing a compound selected from (R)-(+)-5-(p-cyanophenyl)-5,6,7,8-tetrahydroimidazo[1,5-a]pyridine and a pharmaceutically acceptable salt thereof, and wherein very preferably said pharmaceutically acceptable salt is the phosphate salt thereof, and further preferably the (R)-(+)-5-(p-cyanophenyl)-5,6,7,8-tetrahydroimidazolium[1,5-a]pyridine dihydrogen phosphate. The inventive processes comprise the steps of: (i) reacting racemic 5-(p-cyanophenyl)-5,6,7,8-tetrahydroimidazo[1,5-a]pyridine with a (−)-O,O'-acylated L-tartaric acid, in particular (−)-O,O'-dibenzoyl-L-tartaric acid to form the diastereomeric (R)-(+)-5-(p-cyanophenyl)-5,6,7,8-tetrahydroimidazo[1,5-a]pyridine dibenzoyl-L-tartrate salt; and (ii) recrystallizing at least once the tartrate salt obtained in step i; and (iii) liberating the free base (R)-(+)-5-(p-cyanophenyl)-5,6,7,8-tetrahydroimidazo[1,5-a]pyridine by adding a base to a solution of said tartrate salt obtained in step ii; and optionally (iv) forming a pharmaceutically acceptable salt by reacting said free base with an acid, preferably with phosphoric acid ($H_3PO_4$). In one embodiment, said (i) reacting racemic 5-(p-cyanophenyl)-5,6,7,8-tetrahydroimidazo[1,5-a]pyridine with a (−)-O,O'-acylated L-tartaric acid, in particular (−)-O,O'-dibenzoyl-L-tartaric acid to form the diastereomeric (R)-(+)-5-(p-cyanophenyl)-5,6,7,8-tetrahydroimidazo[1,5-a]pyridine dibenzoyl-L-tartrate salt is effected in an alcoholic solution, preferably in a solution of ethanol, at a temperature of below about 50° C., preferably of below about 45° C., and further preferably of below about 40° C. In one embodiment, said (ii) recrystallizing at least once the tartrate salt obtained in step (i) is effected in an aqueous-alcoholic solution, preferably in an aqueous ethanolic solution, wherein preferably the ratio of water:ethanol is of about 2.4: about 10.

In one embodiment, the process for preparing a compound selected from (R)-(+)-5-(p-cyanophenyl)-5,6,7,8-tetrahydroimidazo[1,5-a]pyridine and a pharmaceutically acceptable salt thereof of the invention does not comprise a step of chiral resolution of 5-(p-cyanophenyl)-5,6,7,8-tetrahydroimidazo[1,5-a]pyridine (fadrozole) by means of chiral preparative HPLC, wherein preferably said process for preparing a compound selected from (R)-(+)-5-(p-cyanophenyl)-5,6,7,8-tetrahydroimidazo[1,5-a]pyridine and a pharmaceutically acceptable salt thereof of the invention does not comprise a step of chiral resolution of 5-(p-cyanophenyl)-5,6,7,8-tetrahydroimidazo[1,5-a]pyridine (fadrozole) by means of chiral HPLC. Such step of chiral resolution by means of chiral HPLC can typically comprise (i) repetitive chiral HPLCs on low capacity columns or (ii) preparative HPLC on high capacity column.

In a preferred embodiment, the process of the invention yields (R)-(+)-5-(p-cyanophenyl)-5,6,7,8-tetrahydroimidazo[1,5-a]pyridine and its pharmaceutically acceptable salts thereof, in particular the phosphate salt thereof, further preferably the (R)-(+)-5-(p-cyanophenyl)-5,6,7,8-tetrahydroimidazolium[1,5-a]pyridine dihydrogen phosphate, with an ee of the (R) form higher than or equal to 97%, preferably higher than or equal to 98%, more preferably higher than or equal to 99%, and again more preferably higher than or equal to 99.5%, again more preferably higher than or equal to 99.8%, e.g. 99.9%.

In a further preferred embodiment, the process of the invention yields (R)-(+)-5-(p-cyanophenyl)-5,6,7,8-tetrahydroimidazo[1,5-a]pyridine and its pharmaceutically acceptable salts thereof, in particular the phosphate salt thereof, further preferably (R)-(+)-5-(p-cyanophenyl)-5,6,7,8-tetrahydroimidazolium[1,5-a]pyridine dihydrogen phosphate, wherein said (R)-(+)-5-(p-cyanophenyl)-5,6,7,8-tetrahydroimidazo[1,5-a]pyridine and its pharmaceutically acceptable salts thereof inhibit aromatase activity in the cell-free human recombinant aromatase enzyme assay described in Example 8 with an $IC_{50}$ of of 700 nM or more, preferably 750 nM or more, more preferably 800 nM or more, more preferably 850 nM or more, more preferably 900 nM or more, more preferably 950 nM or more, more preferably 1000 nM or more, more preferably 1050 nM or more, more preferably 1100 nM or more, more preferably 1150 nM or more, more preferably 1200 nM or more, more preferably 1250 nM or more, more preferably 1300 nM or more, more preferably 1350 nM or more, more preferably 1400 nM or more, more preferably 1450 nM or more, more preferably 1500 nM or more, more preferably 1550 nM or more, most preferably at least 1600 nM, e.g. 1610 nM or 1620 nM or 1630 nM or 1640 nM or 1650 nM or more.

The inventive processes, thus, utilize crystallization to obtain (R)-(+)-5-(p-cyanophenyl)-5,6,7,8-tetrahydroimidazo[1,5-a]pyridine and its pharmaceutically acceptable salts thereof, and very preferably its phosphate salt thereof, and again further the (R)-(+)-5-(p-cyanophenyl)-5,6,7,8-tetrahydroimidazolium[1,5-a]pyridine dihydrogen phosphate, in exceptional high chiral purity for commercial pharmaceutical use. On a commercial scale, crystallization is much more advantageous being more economical than chromatographic resolution by allowing for larger batch preparation, less expensive equipment and facilities, and not requiring specialized expertise.

In one aspect, there is provided a pharmaceutical composition comprising (R)-(+)-5-(p-cyanophenyl)-5,6,7,8-tetrahydroimidazo[1,5-a]pyridine or a pharmaceutically acceptable salt thereof, in particular a phosphate salt, more preferably the (R)-(+)-5-(p-cyanophenyl)-5,6,7,8-tetrahydroimidazolium[1,5-a]pyridine dihydrogen phosphate, as described herein in admixture with at least one pharmaceutically acceptable excipient.

In one embodiment, said pharmaceutical composition is provided in the form of tablets, pills, dispersible granules, cachets, capsules, powders, lozenges, suppositories or retention enemas.

EXAMPLES

Equipment, Materials and Methods
Specific Optical Rotation $[\alpha]_D$

The Specific Optical Rotation $[\alpha]_D$ measurements were performed in solution using the sodium D-line at 589.3 nm of a standard Perkin Elmer Polarimeter 343. For the measurement 1 gram of (R)-(+)-5-(p-cyanophenyl)-5,6,7,8-tetrahydroimidazo[1,5-a]pyridine-dihydrogen-phosphate was dissolved in 100 ml of the respective solvent and this solution was transferred in an optical cuvette of 1 decimeter length. The measurement was done at a temperature of 20° C. or 25° C., respectively. The Specific Optical Rotation $[\alpha]_D$ is calculated by the formula 100×α/(l×c) where: α=observed rotation in degrees; l=cell path length in decimeters; c=concentration in grams per 100 ml.
Elemental Analysis Elemental analysis was performed on standard equipment (e.g. vario EL cube elemental analyzer) and the values for carbon, hydrogen and nitrogen were determined.
Chiral HPLC The chiral HPLC was performed on an Agilent 1100 series LC22 instrument with the following column specifications and conditions:
Column: Chiralpack AD-H, granulometry: 5 µm, 250×4.6 mm; no. ADH0CE-TF087
Mobile phase: Ethanol+0.1% diethylamine (DEA)
Detector wavelength: 230 nm
Oven temperature: 25° C.
Flow rate: 0.5 mL/min
Injection volume: 5 µL
Sample preparation: 0.5 mg/mL in Ethanol+0.1% DEA
XRPD The X-ray powder diffraction studies were performed using a Bruker AXS D2 PHASER in Bragg-Brentano configuration. Using a Cu anode at 30 kV, 10 mA; sample stage standard rotating; monochromatisation by a Kβ-filter (0.5% Ni). Slits: fixed divergence slits 1.0 mm (=0.61°), primary axial Soller slit 2.5°, secondary axial Soller slit 2.5°. Detector: Linear detector LYNXEYE with receiving slit 5° detector opening. The standard sample holder (0.1 mm cavity in (510) silicon wafer) had a minimal contribution to the background signal. Measurement conditions: scan range 5 to 45° 2theta, sample rotation 5 rpm, 0.5s/step, 0.010°/step, 3.0 mm detector slit; and all measuring conditions were logged in the instrument control file. As system suitability, corundum sample A26-826-S (NIST standard) was measured daily.

The software used for data collection was Diffrac.Commander v2.0.26. Data analysis was done using Diffrac.Eva v1.4. No background correction or smoothing was applied to the patterns.
Single Crystal X-Ray Analysis Single crystals of (R)-(+)-5-(p-cyanophenyl)-5,6,7,8-tetrahydroimidazolium[1,5-a]pyridine-dihydrogen-phosphate were grown using a n-propanol/water mixture as solvent. A suitable single crystal was taken out of the mother liquor, immediately coated with high viscosity oil, cut to size and mounted on a Mitagen Microloop and shock frozen to 150 K. The measurement was performed on a Bruker D8 Quest instrument with MoKα radiation, using φ-scans and ω-scans. The molecular structure was subsequently solved by direct method (SHELXT software). All non-hydrogen atoms were refined with anisotropic temperature factors. On the completed model, Bijovet analysis was performed to determine the absolute configuration.
TGA/DSC The thermogravimetric analysis and differential scanning calorimetry (TGA/DSC) studies were performed using a Mettler Toledo TGA/DSC1 STARe System with a 34-position auto sampler. The samples were made using Al crucibles (40 µL; pierced). Typically 5-10 mg of sample was loaded into a pre-weighed Al crucible and was kept at 30° C. for 5 minutes, after which it was heated at 10° C./min from 30° C. to 350° C. A nitrogen purge of 40 ml/min was maintained over the sample. The software used for data collection and evaluation was STARe Software v12.10 build 5937. No corrections were applied to the thermogram.
DSC The DSC studies were performed using a Mettler Toledo DSC STARe System. The samples were made using Al crucibles (40 µL; pierced). Typically 1-8 mg of sample was loaded onto a pre-weighed Al crucible and was kept at 30° C. for 5 minutes, after which it was heated at 10° C./min from 30° C. to 350° C. and kept at 350° C. for 1 minute. A nitrogen purge of 40 ml/min was maintained over the sample. As system suitability check Indium and Zinc were used as references. The software used for data collection and evaluation was STARe Software v12.10 build 5937. No corrections were applied to the thermogram.
DVS The Dynamic Vapour Sorption (DVS) studies were performed using a Surface Measurement Systems Ltd. DVS-1 No Video. The sample was loaded into a balance pan, typically 20-30 mg, and equilibrated at 0% RH. After the material was dried, the RH was increased with 10% per step for 1 hour per increment, ending at 95% RH. After completion of the sorption cycle, the sample was dried using the same method. The software used for data collection was DVSWin v3.01 No Video. Data analysis was performed using DVS Standard Analysis Suite v6.3.0 (Standard).
Solubility The solubility was determined using the shake-flask method; the solubility was visually determined at 20° C. The listed solvents were added stepwise to 10 mg of compound, with 15 minutes in between additions, until complete dissolution was obtained or a solubility of less than 0.05 mg/ml was reached.
High Throughput Experimentation High throughput experimentation was performed in well-plate format using a Freeslate Core Module 2 in crystallization configuration equipped with a Julabo FPSO for temperature control of the cooling crystallization experiments.
Solid Dispense System Solids were dispensed using a Freeslate Core Module Protégé Solid Dispense System in classic and SV-hopper configuration with a Sartorius balance. Hoppers that were used were 25 ml classic hoppers with 8 mm valve size and 4 to 3 mm funnel size, 10 ml classic hoppers with 8 mm valve size and 4 to 3 mm funnel size and SV hoppers with standard 4 ml glass vials.

Racemic 5-(p-cyanophenyl)-5,6,7,8-tetrahydroimidazo[1,5-a]pyridine

The title compound (fadrozole) may be prepared e.g., according to the procedure described by L. J. Browne et al. (J. Med. Chem. 1991, 34, 725.) or obtained by commercial suppliers such as Sigma-Aldrich.

Example 1

Diastermomeic Salt Screening with racemic 5-(p-cyanophenyl)-5,6,7,8-tetrahydroimidazo[1,5-a]pyridine 100 mg (1.0 eq) of the title compound were dissolved in isopropanol, followed by addition of a solution of chiral acid (0.5 eq) in isopropanol (0.5 mL). The result of the screening is summarized in Table 2.

TABLE 2

Summary of enantioselective salt crystallization experiments

| Chiral acid | Formula MW | Condition | Result |
|---|---|---|---|
| L-(+)-Tartaric acid CAS: 87-69-4 | $C_4H_6O_6$ 150.09 | 10 V 5 V 0.5 eq | No crystallization Formation of a gum |
| (-)-O,O'-Dibenzoyl-L-tartaric acid monohydrate CAS: 62708-56-9 | $C_{18}H_{14}O_8 \cdot H_2O$ 376.34 | 10 V 0.5 eq | Crystallization ee: 55% |
| L-(-)-Malic acid CAS: 97-67-6 | $C_4H_6O_5$ 134.09 | 10 V 5 V 0.5 eq | No crystallization |
| L-(+)-Mandelic acid CAS: 17199-29-0 | C8H8O3 152.15 | 10 V 5 V 0.5 eq | No crystallization |
| (1S-(+)-10-Camphorsulfonic acid CAS: 3144-16-9 | $C_{10}H_{16}O_4S$ 223.30 | 10 V 5 V 0.5 eq | No crystallization |

Example 2

Salt Screening with (R)-(+)-5-(p-cyanophenyl)-5,6,7,8-tetrahydroimidazo[1,5-a]pyridine General Procedure:

The title compound (free base) was dissolved in ethanol (at 100 g/L) at 35° C., followed by addition of the acid at the same temperature. The resulting mixture was cooled to 10° C. at a cooling rate of −20° C./h and the precipitate (if any) was filtered off, washed with ethanol and dried under reduced pressure (at 50° C.).

The result of the salt screening is summarized in Tables 3 to 5.

TABLE 3

Summary of salt screening experiments with ethanol as solvent

| Salt forming acid | Stoichiometry (eq) | Result |
|---|---|---|
| fumaric acid | 1:1 | oil |
| tartaric acid | 1:1 | solid |
| sulfuric acid | 1:1 | oil |
| phosphoric acid* | 1:1 | solid |
| adipic acid | 1:1 | oil |
| glucuronic acid* | 1:1 | no salt isolated |
| glutaric acid | 1:1 | oil |
| malic acid | 1:1 | oil |

TABLE 3-continued

Summary of salt screening experiments with ethanol as solvent

| Salt forming acid | Stoichiometry (eq) | Result |
|---|---|---|
| malonic acid | 1:1 | oil |
| fumaric acid | 1:2 | solid |
| tartaric acid | 1:2 | solid |
| adipic acid | 1:2 | oil |
| glutaric acid | 1:2 | oil |
| malic acid | 1:2 | oil |
| malonic acid | 1:2 | oil |

*slurry

TABLE 4

Summary of salt screening experiments with methanol as solvent

| Counter ion | Stoichiometry (eq) | Result |
|---|---|---|
| fumaric acid | 1:1 | solid |
| tartaric acid | 1:1 | oil |
| sulfuric acid | 1:1 | oil |
| phosphoric acid* | 1:1 | solid |
| adipic acid | 1:1 | oil |
| glucuronic acid* | 1:1 | oil |
| glutaric acid | 1:1 | oil |
| malic acid | 1:1 | oil |
| malonic acid | 1:1 | oil |
| fumaric acid | 1:2 | solid |
| tartaric acid | 1:2 | oil |
| adipic acid | 1:2 | counter ion salt |
| glutaric acid | 1:2 | oil |
| malic acid | 1:2 | oil |
| malonic acid | 1:2 | oil |

*slurry

With the phosphate salt, the tartrate salt and the fumarate salt that were obtained as solids, a solid state characterization according to Table 5 was performed.

TABLE 5

Solid state characterization

| Criterion | Phosphate salt | Tartrate salt | Fumarate salt |
|---|---|---|---|
| Crystallinity | good | good | good |
| Water solubility | good | good | good |
| Polymorph tendency (XRPD) | Not observed | Not observed | 2 polymorphs observed |
| Hygroscopicity (DVS) | low | high | medium |
| Solid phase transition (XRPD) | Not observed | Not observed | 2 polymorphs observed |
| Solvation | anhydrous | anhydrous | anhydrous |
| Melting point (DSC/TGA) | 189° C. | 150° C. | 120° C. |

Example 3

Preparation of (R)-(+)-5-(p-cyanophenyl)-5,6,7,8-tetrahydroimidazolium[1,5-a]pyridine dihydrogen phosphate (Crystalline Form I)

Step 1: Preparation of (R)-(+)-5-(p-cyanophenyl)-5,6,7,8-tetrahydroimidazolium[1,5-a]pyridine dibenzoyl-L-tartrate In a 10 L reactor were loaded at 20° C. racemic 5-(p-cyanophenyl)-5,6,7,8-tetrahydroimidazo[1,5-a]pyridine (328 g, =1.0 eq) and ethanol (2.3 L). The mixture was heated to 40° C. then a solution of (−)-O,O-dibenzoyl-L-tataric acid (276.4 g, 0.5 eq) in ethanol (1 L) was added. The mixture was maintained at 40° C. for 1h, then cooled to 20° C. over a period of 2h, maintained for 1h at this temperature, then cooled to 10° C. over a period of 0.5 h and finally maintained at 10° C. overnight. The precipitate was subsequently filtered off and the filter cake was washed with cold (0° C.) ethanol (1 L) to afford the title compound as a white humid powder (485 g, =413.7 g estimated dry, by loss on drying, 48.4%, ee=87%).

Step 2: Recrystallization of (R)-(+)-5-(p-cyanophenyl)-5,6,7,8-tetrahydroimidazolium[1,5-a]pyridine dibenzoyl-L-tartrate In a 10 L reactor were loaded at 20° C. (R)-(+)-5-(p-cyanophenyl)-5,6,7,8-tetrahydroimidazolium[1,5-a]pyridine dibenzoyl-L-tartrate (485 g, ee=87%, =413.7 g estimated dry, by loss on drying, =1.0 eq) obtained from step 1, ethanol (10 L, 24 V) and water (2.4 L, 6V). The resulting mixture was heated to reflux, whereupon a solution was formed. The solution was then cooled to 50° C. and maintained at this temperature for 1 h. Subsequently, the mixture was allowed to cool to 10° C. over a period of 2 h and then maintained at this temperature overnight. The precipitate was filtered off and the filter cake was washed with cold (0° C.) ethanol (1.2 L). The product was dried under reduced pressure at 40° C. to afford the title compound as a white powder (294.8 g, 71%, single enantiomer). Enantiomeric Excess: >99.9% as determined by HPLC

Step 3: Preparation of (R)-(+)-5-(p-cyanophenyl)-5,6,7,8-tetrahydroimidazo[1,5-a]pyridine (Free Base)

In a 2 L reactor were loaded (R)-(+)-5-(p-cyanophenyl)-5,6,7,8-tetrahydroimidazolium[1,5-a]pyridine dibenzoyl-L-tartrate (177 g, single enantiomer) obtained from step 2 and dichloromethane (1.77 L, 10 V). T en, a solution of $Na_2CO_3$ (71 g, 2.2 eq) in water (875 mL) was added. After 0.25 h stirring at room temperature, the mixture was decanted. The liquid phases thus obtained were limpid and the aqueous phase had a pH of 8-9. The organic phase was washed with water (2×875 mL) and then concentrated under vacuum. The residue was dissolved in ethanol and again concentrated under vacuum to afford the title compound (70 g, quant.) as an oil which solidified upon standing.

Step 4: (R)-(+)-5-(p-cyanophenyl)-5,6,7,8-tetrahydroimidazolium[1,5-a]pyridine dihydrogen phosphate In a 1 L reactor were loaded (R)-(+)-5-(p-cyanophenyl)-5,6,7,8-tetrahydroimidazo[1,5-a]pyridine (94 g, 1.0 eq) and ethanol (564 mL) and the mixture was heated to 35° C. The solution was filtered and the reactor was rinsed with ethanol (94 mL). A solution of $H_3PO_4$ (97 g, 85% wt/wt in $H_2O$) in ethanol (235 mL) was added at the same temperature, rinsing with ethanol (47 mL). After stirring for 1 h at 35° C., the mixture was cooled to 10° C. (at a rate of −20° C./h) and kept at this temperature for 10 h. The resulting solid was filtered off and the filter cake was washed with cold (10° C.) ethanol (3×94 mL). After drying at 50° C. under reduced pressure, the title compound was obtained as a white, crystalline, free flowing powder (100 g, 74%).

Figure 3:
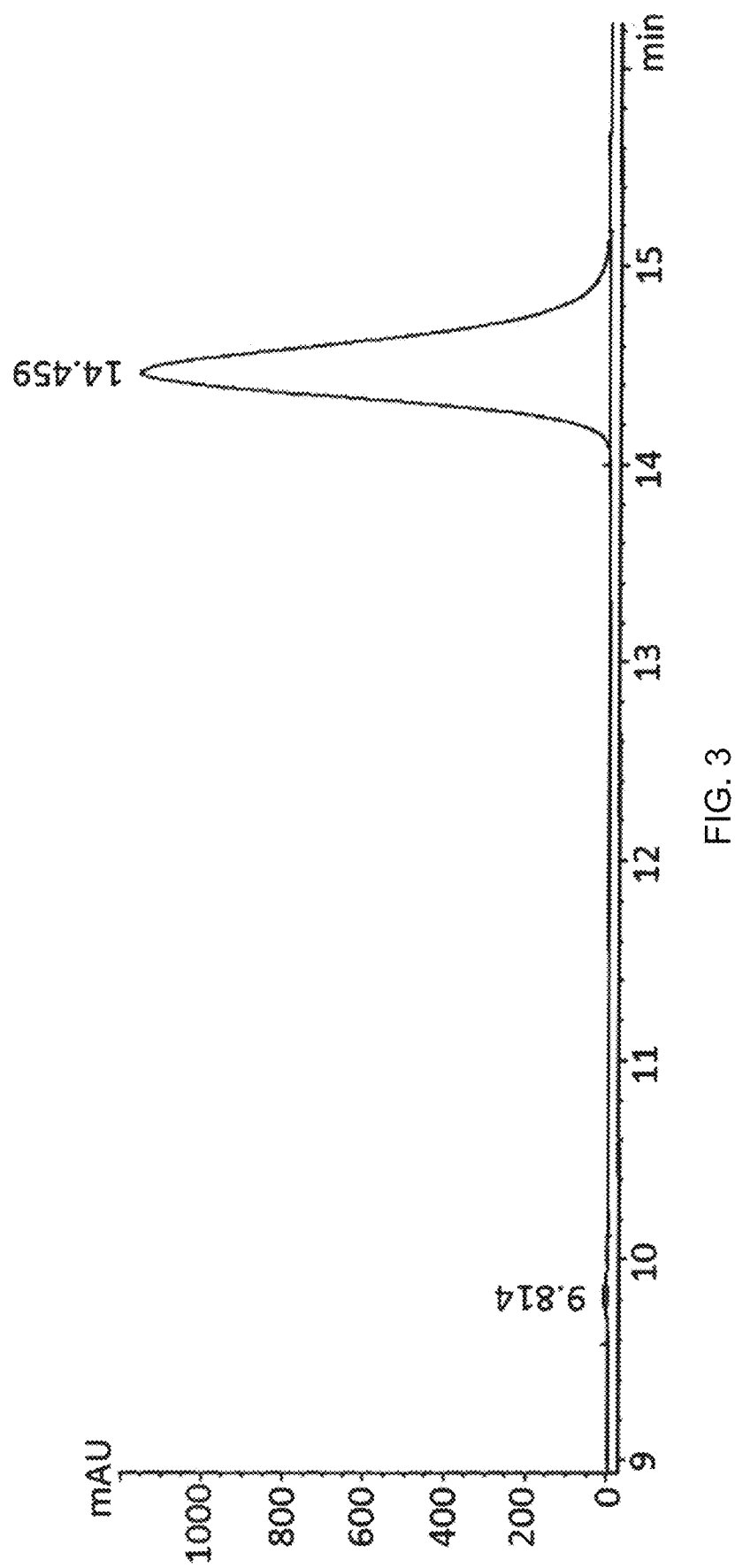
FIG. 3: Chiral purity of (R)-(+)-5-(p-cyanophenyl)-5,6,7,8-tetrahydroimidazolium[1,5-a]pyridine dihydrogen phosphate determined by high pressure liquid chromatography (HPLC). The chromatogram demonstrates an enantiomeric excess of the R-(+) enantiomer (retention time 14.459 min) of higher than 99.9% ee (retention time of the S-(−)-enantiomer: 9.814 min).
Figure 6:
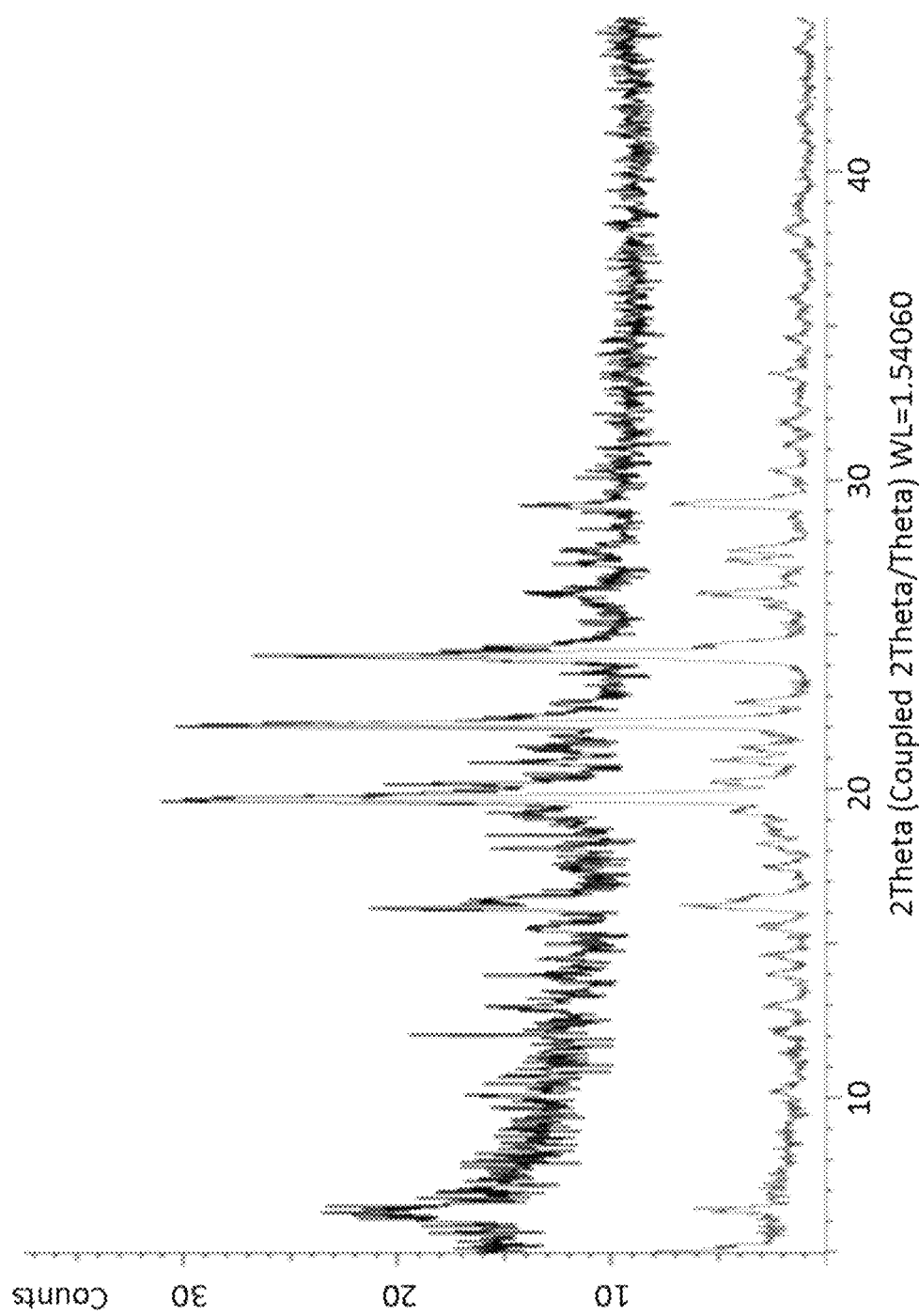
FIG. 6: X-ray powder diffraction (XRPD) diffractograms of (R)-(+)-5-(p-cyanophenyl)-5,6,7,8-tetrahydroimidazolium[1,5-a]pyridine dihydrogen phosphate measured before (upper pattern) and after (lower pattern) DVS cycles. The overlayed diffractograms indicate that DVS treatment does not affect the reflection patterns respectively the crystal form.

XRPD: see FIG. 1 and Table 1
Melting Point: 189° C. as determined by TGA/DSC (FIG. 2).
Enantiomeric Excess: >99.9% (FIG. 3). The chiral HPLC for the determination of the enantiomeric excess of the preparation featured a retention time (tr) of 14.459 min for the R-(+)-enantiomer and 9.814 Min for the S-(−)-enantiomer.
Absolute configuration: R-(+)-on carbon 5 as determined by single crystal X-ray.
Specific optical rotation ($CH_3CN:H_2O$ 1:1 (v/v)): $[\alpha]_D^{20}$=+98.1
Hygroscopicity: 1.0% at ≥90% relative humidity (RH) as determined by DVS. Water uptake is reversible and crystalline form does not change upon DVS treatment (FIGS. 4 to 6). Mass loss upon heating up until 225° C. is 1.4% as determined by TGA/DSC (FIG. 2). The crystals of (R)-(+)-5-(p-cyanophenyl)-5,6,7,8-tetrahydroimidazolium[1,5-a]pyridine dihydrogen phosphate were further characterized by their elemental analysis, which is in accordance with the values calculated from the molecular formula $C_{14}H_{16}N_3O_4P$ (MW:321.27): C 52.4%; H 5.1%; N 13.03%.

Example 4

Preparation of (R)-(+)-5-(p-cyanophenyl)-5,6,7,8-tetrahydroimidazolium[1,5-a]pyridine-chloride from (R)-(+)-5-(p-cyanophenyl)-5,6,7,8-tetrahydro-imidazolium[1,5-a]pyridine dihydrogen phosphate Via the Free Base (R)-(+)-5-(p-cyanophenyl)-5,6,7,8-tetrahydro-imidazolium[1,5-a]pyridine dihydrogen phosphate (1000 mg, 3.11 mmol,) as prepared in Example 3 was suspended in $Et_2O$ (30 ml) and extracted with saturated aqueous $NaHCO_3$ solution (30 ml). The aqueous layer was extracted with diethyl-ether (2×20 ml) and the combined organic layers were washed with brine (10 ml) and distilled water (10 ml), dried over $Na_2SO_4$, filtered and evaporated to obtain the free base (R)-(+)-5-(p-cyanophenyl)-5,6,7,8-tetrahydroimidazo[1,5-a]pyridine as a white solid which was dried in vacuum over night at 50° C. (530 mg).
Melting point: 101-102° C.; Specific optical rotation (ethanol): $[\alpha]_D^2$=+127.3;

The so obtained (R)-(+)-5-(p-cyanophenyl)-5,6,7,8-tetrahydroimidazo[1,5-a]pyridine (100 mg, 0.447 mmol, 1 eq) was dissolved in methylene chloride (2.2 ml) and HCl (2 M in diethylether, 0.34 ml, 0.76 mmol, 1.5 eq) was added and the mixture was stirred for 30 minutes at RT, then evaporated and dried under vacuum at 80° C. (R)-(+)-5-(p-cyanophenyl)-5,6,7,8-tetrahydro-imidazolium[1,5-a]pyridine chloride was isolated as a crystalline solid.
Melting point: 240-243° C.; Specific optical rotation (ethanol): $[\alpha]_D^{20}$=+104.8; Specific optical rotation ($CH_3CN:H_2O$ 1:1 (v/v)): $[\alpha]_D^2$=+124.4.

Example 5

Hygroscopicity of (R)-(+)-5-(p-cyanophenyl)-5,6,7,8-tetrahydro-imidazolium[1,5-a]pyridine-dihydrogen phosphate Compared to (R)-(+)-5-(p-cyanophenyl)-5,6,7,8-tetrahydro-imidazolium[1,5-a]pyridine-chloride 100 mg samples of the two crystalline salts were stored in open flasks for 24 hours side by side at room temperature in unconditioned ambient air and weight measurements occurred at time 0 and after 24 hours (Table 6). (R)-(+)-5-

(p-cyanophenyl)-5,6,7,8-tetrahydro-imidazolium[1,5-a]pyridine dihydrogen phosphate shows a weight increase of 0.57% and is considered to be non-hygroscopic as compared to the significant hygroscopicity of the corresponding (R)-(+)-5-(p-cyanophenyl)-5,6,7,8-tetrahydroimidazolium[1,5-a]pyridine chloride evidenced by the 13.1% weight increase.

TABLE 6

Comparison of hygroscopic properties

| Time | Phosphate Salt | | Chloride Salt | |
|---|---|---|---|---|
| | Absolute weight | Weight increase | Absolute weight | Weight increase |
| 0 hours | 103.3 mg | — | 100.1 mg | — |
| 24 hours | 103.9 mg | 0.57% | 113.2 mg | 13.1% |

Example 6

Shake-Flask Solubility Study of (R)-(+)-5-(p-cyanophenyl)-5,6,7,8-tetrahydroimidazolium[1,5-a]pyridine dihydrogen phosphate A shake-flask solubility study was performed on the material according to U.S. Pharmacopoeia (USP) specifications. A set of pharmaceutically accepted process solvents with different functional groups has been used to determine the shake-flask solubility. The solvents were allowed to evaporate at 0-100 mbar at room temperature overnight. All solids have then been subsequently analysed using XRPD. The results of this study can be found in Table 7 below.

TABLE 7

Shake-flask solubility results of the different batches

| Sample code | Solvent | Solubility (mg/ml) | USP classification |
|---|---|---|---|
| DF1181-5-S1 | Methanol | 112-1120 | Freely soluble |
| DF1181-5-S2 | Dichloromethane | <0.10 | Practically insoluble |
| DF1181-5-S3 | Methyl tert-butyl ether | <0.11 | Practically insoluble |
| DF1181-5-S4 | Acetone | <0.09 | Practically insoluble |
| DF1181-5-S5 | Ethyl acetate | <0.09 | Practically insoluble |
| DF1181-5-S6 | Ethanol | 0.1-1.0 | Very slightly soluble |
| DF1181-5-S7 | Acetonitrile | <0.11 | Practically insoluble |
| DF1181-5-S8 | n-Heptane | <0.11 | Practically insoluble |
| DF1181-5-S9 | Water | >1000 | Freely soluble |
| DF1181-5-S10 | Toluene | <0.10 | Practically insoluble |
| DF1181-5-S11 | Acetic acid | 118-1180 | Freely soluble |

The material is very soluble in water, freely soluble in methanol and acetic acid, very slightly soluble in ethanol and practically insoluble in the other tested solvents. In Table 8 the XRPD results of the performed measurements on either the solids of the slurry or the solids of the solution after evaporation are given.

TABLE 8

XRPD results after solubility determination

| Sample code | XRPD |
|---|---|
| DF1181-5-S1 | Form I - Conform starting material |
| DF1181-5-S2 | Form I - Conform starting material |
| DF1181-5-S3 | Form I - Conform starting material |
| DF1181-5-S4 | Form I - Conform starting material |
| DF1181-5-S5 | Form I - Conform starting material |
| DF1181-5-S6 | Form I - Conform starting material |
| DF1181-5-S7 | Form I - Conform starting material |
| DF1181-5-S8 | Form I - Conform starting material |
| DF1181-5-S9 | Form I - Conform starting material |
| DF1181-5-S10 | Form I - Conform starting material |
| DF1181-5-S11 | Amorphous |

No new polymorphic form was obtained after evaporation of the solvents, except for acetic acid (amorphous), confirming the exceptional stability of crystalline form I.

Example 7

Polymorph Study on (R)-(+)-5-(p-cyanophenyl)-5,6,7,8-tetrahydroimidazolium[1,5-a]pyridine dihydrogen phosphate Solvents and co-solvents were added in different ratios. The different ratios were 100% solvent and 0% co-solvent, 80% solvent and 20% co-solvent, 60% solvent and 40% co-solvent, 40% solvent and 60% co-solvent, 20% solvent and 80% co-solvent and 5% solvent and 95% co-solvent, subsequently. Table 9 shows the layout of the study conditions and the respective XRPD conclusions on polymorphic forms.

TABLE 9

Layout of the 96-well polymorph study master plate

| Well position | Solvent | Co-solvent | XRPD |
|---|---|---|---|
| 1-6 | Formic acid | Water | Form I |
| 7-12 | 2-Butanone | n-Heptane | Form I |
| 13-18 | Acetic acid | Water | Form I |
| 19-24 | Cyclohexanone | n-Heptane | Form I |
| 25-30 | Methanol | Water | Form I |
| 31-36 | Ethylacetate | n-Heptane | Form I |
| 37-42 | Ethanol | Water | Form I |
| 43-48 | Isopropyl acetate | n-Heptane | Form I |
| 49-54 | 2-Propanol | Water | Form I |
| 55-60 | Cyclopentyl methyl ether | n-Heptane | Form I |
| 61-66 | Acetone | Water | Form I |
| 67-72 | Toluene | n-Heptane | Form I |
| 73-78 | Acetonitrile | Water | Form I |
| 79-84 | Cyclohexane | n-Heptane | Form I |

TABLE 9-continued

Layout of the 96-well polymorph study master plate

| Well position | Solvent | Co-solvent | XRPD |
|---|---|---|---|
| 85-90 | Tetrahydrofuran | Water | Form I |
| 91-96 | Chlorobenzene | n-Heptane | Form I |

The starting material was dispensed (30 mg) in a 96-well plate ("master plate") using a Freeslate CM Protégé solid dispense system. After solid dispense the well plate was transferred to the Freeslate Core Module 2 for liquid dispenses (solvent+co-solvent total=800 μL). The master plate was allowed to stir for 2 h at 50° C. An aliquot of the samples in the master plate was transferred to a cooling crystallization plate via a hot filtration plate. The samples in the cooling plate were then allowed to cool from 50° C. to 10° C. over a period of 5 hours using a cubic cooling rate. None of the wells contained solids, so to simulate evaporative crystallization the solvents were allowed to evaporate at 0-100 mbar at RT. All of the formed solids were analysed using XRPD. All diffractograms were compared with the reference diffractogram as outlined in FIG. 1 by overlaying the respective diffractograms (FIG. 6). In this study, only one polymorph of the title compound, form I, could be identified having the described very beneficial and surprising properties. This finding seems to confirm that crystallization is not only a function of salt selection but also of crystallization process conditions leading to the inventive form I of the (R)-(+)-5-(p-cyanophenyl)-5,6,7,8-tetrahydroimidazolium[1,5-a]pyridine dihydrogen phosphate (P. Heinrich Stahl (Editor), Camille G. Wermuth (Editor); Handbook of Pharmaceutical Salts: Properties, Selection, and Use, 2nd Revised Edition, March 2011, Wiley-VCH, ISBN: 978-3-90639-051-2).

Example 8

Assessment of Aromatase and Aldosterone Synthase Inhibition by (R)-(+)-5-(p-cyanophenyl)-5,6,7,8-tetrahydroimidazolium[1,5-a]pyridine dihydrogen phosphate Human NCI-H295R Cell Assay for Aldosterone Synthase (CYP11B2) and Aromatase (CYP19) Activities NCI-H295R cells, a continuous cell line derived from an invasive primary adrenocortical carcinoma were obtained from CLS cell line services GmbH (catalog No. 300483). Because NCI-H295R cells produce both aldosterone and estradiol, they enable measuring aldosterone synthase activity and aromatase activity under identical conditions. Prior to being used for the assays the cells were maintained in DMEM/Ham's medium with 15 mM HEPES and 1.2 g $NaHCO_3$ supplemented with 5% steroid-free serum replacement, Panexin BMM (PAN Biotech, Aldenbach, Germany; cat. no. P04-9515A2), 1% Penicillin/Streptomycin, 1.25% L-Glutamine, and 6.25 μg/ml insulin, 6.25 ng/ml selenium, 5.35 μg/ml linoleic acid and 1.25 mg/ml bovine serum albumin. The cells were maintained at 37° C. under an atmosphere of 95% air/5% $CO_2$. For the assays the cells were sub-cultured at a density of $5\times10^5$ cells per well in 24-well plates and grown until 50-60% confluency (48 h). The growth medium then was replaced with 500 μl serum-free DMEM:Ham's F12 containing the test compound dissolved in ethanol/water 1:1 (v/v) so that the final concentration in the assay consisted of 0.5% ethanol. Six concentrations were evaluated, and control samples with no compound were supplemented with 0.5% ethanol. The cells with compound were incubated at 37° C. under 95% air/5% $CO_2$ for 6h. After which the supernatant was removed and stored at −20° C. until analysis. After the supernatant was removed the cells were evaluated to assure viability by optical evaluation utilizing phase contrast microscopy examination for morphological changes and by the resazurin method which measures the conversion of resazurin into a fluorescent end product resorufin. Non-viable cells lack the metabolic capacity to make the conversion. The conversion was quantified by measuring the fluorescence at 544 nm/590 nm (extinction/emission) respectively using a Wallac 1420 Multiple Counter Victor Fluorometer/Luminator (Perkin Elmer, Wlatham, Mass.).

Quantification of aldosterone concentration as a measure of aldosterone synthase activity was accomplished by LC-MS as follows. Prior to analysis acetonitrile was used to precipitate the sample protein and following centrifugation the particle free supernatant was subject to LC-MS. The HPLC system consisted of an Accela U-HPLC pump and Accela Open auto sampler (Thermo Fisher Scientific, Waltham, Mass.). Mass spectrometry was performed using a Q-Exactive MS (Orbitrap) equipped with a heated electrospray (H-ESI) interface connected to a PC running the standard Xcalibur software 2.2 (Thermo Fisher Scientific, Waltham, Mass.). The LC was performed in the gradient mode using acetonitrile with 0.1% formic acid (solvent A) and aqueous 0.1% formic acid solvent B. The pump flow rate was set to 600 μl/min, and separation was performed on a Kinetex Phenyl-Hexyl 2.6 μm, 50×2.1 mm analytical column (Phenomenex, Germany) with a C6-Phenyl, 4×2.0 mm ID pre-column for quantification. As MS tune file a generic tune file was used and as a lock mass for internal calibration the $[M+H]^+$ ion of the disooctyl phthalate (m/z 391.28492) present in the solvent system was used. Full MS-SIM analysis (m/z: 250-400) was applied with the mass resolution of the Orbitrap™ set to 35,000. The sample injection volume was 20 μl for all samples. The results were displayed as ng/ml and inhibition of aldosterone production was expressed as percent inhibition relative to untreated controls i.e., in absence of any inhibitor (Table 10). $IC_{50}$ values were calculated using linear interpolation using the concentrations of test compound and the corresponding percentage inhibition that are immediately above and below 50% as illustrated below:

$$IC_{50}=(50\%-Low_{inh}\%)/(High_{inh}\%-Low_{inh}\%)\times (High_{conc}-Low_{conc})+Low_{conc}$$

where "inh" is inhibition and "conc" is concentration.

TABLE 10

Inhibition of aldosterone production by (R)-(+)-5-(p-cyanophenyl)-5,6,7,8-tetrahydroimidazolium[1,5-a]pyridine dihydrogen phosphate in NCI-H295R cells.

| Concentration (nM) | Mean Inhibition (%) (3 determinations) | Standard Deviation |
|---|---|---|
| 10'000 | 100.0 | 0.0 |
| 1'000 | 100.0 | 0.0 |
| 100 | 100.0 | 0.0 |
| 10[a] | 60.8[c] | 4.0 |
| 1[b] | 8.7[d] | 13.0 |
| 0.1 | −19.6 | 9.9 |

[a]$High_{conc}$ = the lowest concentration of the test item that inhibits by at least 50% (10 nM)
[b]$Low_{conc}$ = the highest concentration of the test item that inhibits less than 50% (1 nM)
[c]$High_{inh}$ = percent inhibition achieved at the $High_{conc}$ of the test item (60.8%)
[d]$Low_{inh}$ = percent inhibition achieved at the $Low_{conc}$ of the test item (8.7%)
$IC_{50}$ = (50% − 8.7%)/(60.8% − 8.7%) × (10 nm − 1 nM) + 1 nM = 8.1 nM
$IC_{50}$ = 8.1 nM for inhibition of aldosterone production (aldosterone synthase activity)

Aromatase activity was measured by quantification of the estradiol concentration in the supernatant from incubation of NCI-H295R cells as described above for determination of aldosterone synthase activity except that much higher concentrations of the inhibitor, as indicated below were used to obtain an IC50. Quantification of estradiol concentration was accomplished using a 17-beta-estradiol ELISA kit from IBL-Hamburg (Hamburg, Germany) according to the manufacturer's instructions. A standard curve was generated by plotting the absorbance of each reference standard (y-axis) against the corresponding log concentration (x-axis). The absorbance of each sample was used to determine the corresponding values by interpolation from the standard curve using GraphPad Prism 5.04 software (GraphPad Software Inc., San Diego, Calif.). An $IC_{50}$ was calculated using the formula described above for the aldosterone synthase data disclosed in Table 11.

TABLE 11

Inhibition of estradiol production by (R)-(+)-5-(p-cyanophenyl)-5,6,7,8-tetrahydroimidazolium[1,5-a]pyridine dihydrogen phosphate in NCI-H295R cells.

| Concentration (µM) | Mean Inhibition (%) (3 determinations) | Standard Deviation |
|---|---|---|
| 1000 | 80.4 | 1.6 |
| 100 | 82.8 | 0.8 |
| 10$^a$ | 68.6$^c$ | 5.3 |
| 1$^b$ | 29.1$^d$ | 8.4 |
| 0.1 | 12.5 | 5.3 |
| 0.01 | −1.5 | 14.8 |

$^a$High$_{conc}$ = the lowest concentration of the test item that inhibits by at least 50% (10 µM)
$^b$Low$_{conc}$ = the highest concentration of the test item that inhibits less than 50% (1 µM)
$^c$High$_{inh}$ = percent inhibition achieved by the High$_{conc}$ of the test item (68.6%)
$^d$Low$_{inh}$ = percent inhibition achieved by the Low$_{conc}$ of the test item (29.1%)
$IC_{50}$ = (50% − 29.1%)/(68.6% − 29.1%) × (10 µM − 1 µM) + 1 µM = 5.76 µM or 5760 nM
$IC_{50}$ = 5760 nM for inhibition of estradiol production (aromatase activity)

Cell-Free Human Recombinant Aromatase Assay

Aromatase (CYP19) activity was measured using a human CYP19 assay kit (Corning®, Corning, N.Y.; Product #456260) according to the manufacturer's instructions. The assay system utilized a recombinant human enzyme, a fluorometric substrate MFC (7-methyl-4-trifluoro-methyl-Coumarin), and an NADPH regenerating system consisting of glucose-6-phosphate dehydrogenase, NADP$^+$, and glucose-6-phospahate. For determining the concentrations of the test compounds which inhibited the enzyme activity by 50% ($IC_{50}$) eight test concentrations were tested. The test compounds were dissolved in ethanol/water 1:1 (v/v) so that the final ethanol concentration in the assay was 1%. The test compounds at various concentrations along with the NADPH regenerating system were added to 96-well plates. After a 10 min pre-incubation the reaction was started by the addition of pre-warmed enzyme substrate mix and allowed to continue for an additional 30 min at 37° C. The reaction was then stopped by the addition of a solution of 80% acetonitrile and 20% 0.5M Tris base (stop solution). To control for background fluorescence, blank wells (containing no test samples) were also assayed but these wells had the stop solution added prior to the addition of the enzyme substrate mixture. The fluorescent product formed, 7-hydroxy-4-triflouro-methyl-Coumarine (HFC) was detected using a Wallac 1420 Multiple Counter Victor Fluorometer/Luminator (Perkin Elmer, Wlatham, Mass.). The wave lengths for excitation and emission were 405 and 535 nm, respectively. The data was compiled with standard software Wallac 1420 Manager 3.0. In addition to subtraction of the blank well samples as indicated above, each test substance was pre-tested for auto-fluorescence. For this purpose the NADPH generating system (cofactor mix) and the enzyme/substrate-mix were replaced by a comparable mixture of control protein, assay buffer, and test compound solvent. These control samples were then pre-incubated and assayed and as described above. Three independent determinations of the $IC_{50}$ were made from line of best fit plots of % inhibition versus inhibitor concentration (Table 12).

TABLE 12

Inhibition of human recombinant aromatase activity by (R)-(+)-5-(p-cyanophenyl)-5,6,7,8-tetrahydroimidazolium[1,5-a]pyridine dihydrogen phosphate.

| Trial (8 concentrations of inhibitor per trial) | Half-maximal inhibitory concentration $IC_{50}$ (nM) |
|---|---|
| 1 | 1694 |
| 2 | 1557 |
| 3 | 1668 |
| Mean | 1640 |
| Standard deviation | ±72.5 |

Example 9

Assessment of Stability Data for (R)-(+)-5-(p-cyanophenyl)-5,6,7,8-tetrahydroimidazolium[1,5-a]pyridine dihydrogen phosphate Long-term stability data relevant and important for regulatory considerations have been measured. Hereto, various tests as indicated in below Tables 13 to 15 have been conducted at either 25° C. and 60% RH (Table 13), at 30° C. and 65% RH (Table 14), and at 40° C. and 75% RH (Table 15) each test at various time points (initial, after 1, 3 and 6 months or even longer).

It has been shown that (R)-(+)-5-(p-cyanophenyl)-5,6,7,8-tetrahydroimidazolium[1,5-a]pyridine dihydrogen phosphate is very stable over a long and extended period of time, and that in particular long-term stability has been shown with respect to purity, water content and thus hygroscopicity as well as chiral purity under the assessed stability conditions and time periods. Moreover, and importantly, no change of polymorphism was observed at neither assessed condition and time periods.

TABLE 13

Stability data at stability conditions 25° C./60% RH for (R)-(+)-5-(p-cyanophenyl)-5,6,7,8-tetrahydroimidazolium[1,5-a]pyridine dihydrogen phosphate.

| Test | Initial | 1 month | 3 months | 6 months | 9 months | 12 months |
|---|---|---|---|---|---|---|
| Appearance | White powder | White powder | White powder | White powder | White powder | White powder |
| Assay by HPLC, anhydrous, solvent free | 99.9 | 99.5 | 99.8 | 99.6 | 99.7 | 100.3 |

TABLE 13-continued

Stability data at stability conditions 25° C./60% RH for (R)-(+)-5-(p-cyanophenyl)-5,6,7,8-tetrahydroimidazolium[1,5-a]pyridine dihydrogen phosphate.

| Test | Initial | 1 month | 3 months | 6 months | 9 months | 12 months |
|---|---|---|---|---|---|---|
| Purity by HPLC | 99.87 | 99.77 | 99.81 | 99.82 | 99.84 | 99.81 |
| Water content | 0.3 | 0.2 | 0.2 | 0.2 | 0.2 | 0.3 |
| Chiral Purity | >99.5 | >99.5 | >99.5 | >99.5 | >99.5 | >99.5 |
| Polymorph by XRPD | Conform to initial | Conform to initial | Conform to initial | Conform to initial | Conform to initial | Conform to initial |

TABLE 14

Stability data at stability conditions 30° C./65% RH for (R)-(+)-5-(p-cyanophenyl)-5,6,7,8-tetrahydroimidazolium[1,5-a]pyridine dihydrogen phosphate.

| Test | Initial | 1 month | 3 months | 6 months | 9 months | 12 months |
|---|---|---|---|---|---|---|
| Appearance | White powder | White powder | White powder | White powder | White powder | White powder |
| Assay by HPLC, anhydrous, solvent free | 99.9 | 99.6 | 100.1 | 99.6 | 99.6 | 99.5 |
| Purity by HPLC | 99.87 | 99.76 | 99.81 | 99.84 | 99.86 | 99.85 |
| Water content | 0.3 | 0.2 | 0.3 | 0.2 | 0.2 | 0.3 |
| Chiral Purity | >99.5 | >99.5 | >99.5 | >99.5 | >99.5 | >99.5 |
| Polymorph by XRPD | Conform to initial | Conform to initial | Conform to initial | Conform to initial | Conform to initial | Conform to initial |

TABLE 15

Stability data at stability conditions 40° C./75% RH for (R)-(+)-5-(p-cyanophenyl)-5,6,7,8-tetrahydroimidazolium[1,5-a]pyridine dihydrogen phosphate.

| Test | Initial | 1 month | 3 months | 6 months |
|---|---|---|---|---|
| Appearance | White powder | White powder | White powder | White powder |
| Assay by HPLC, anhydrous, solvent free | 99.9 | 99.7 | 100.2 | 99.2 |
| Purity by HPLC | 99.87 | 99.80 | 99.79 | 99.88 |
| Water content | 0.3 | 0.3 | 0.5 | 0.3 |
| Chiral Purity | >99.5 | >99.5 | >99.5 | >99.5 |
| Polymorph by XRPD | Conform to initial | Conform to initial | Conform to initial | Conform to initial |

The invention claimed is:

1. A compound having the structure:

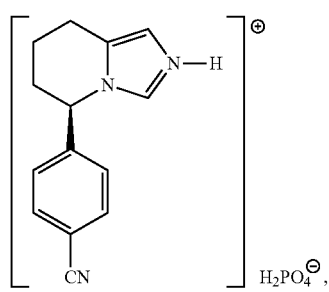

wherein said compound has an enantiomeric excess of the (R) form higher than or equal to 97%.

2. The compound of claim 1, wherein said compound inhibits aromatase activity in a cell-free human recombinant aromatase enzyme assay with an $IC_{50}$ of 700 nM or more.

3. The compound of claim 1, wherein said compound inhibits aldosterone synthase in a NCI-H295R adrenal cell assay with an $IC_{50}$ of 100 nM or less.

4. The compound of claim 1, wherein said compound has a selectivity for aldosterone synthase over aromatase of 50 or more, wherein said selectivity is determined by a ratio of the $IC_{50}$ values for inhibition of aromatase and aldosterone synthase; wherein the $IC_{50}$ values for inhibition of aldosterone synthase and aromatase are both measured in the NCI-H295R adrenal cell assay.

5. The compound of claim 1, wherein said compound is crystalline.

6. The compound of claim 1, wherein said compound is anhydrous.

7. The compound of claim 1, wherein said compound is non-hygroscopic.

8. The compound of claim 1, wherein said compound has a melting point of equal or between 184° C. to 193° C. as determined by thermogravimetry analysis/differential scanning calorimetry.

9. The crystalline compound of claim 5, wherein said crystalline compound has an X-ray powder diffraction pattern comprising 2θ values measured using CuKα radiation: 19.504; 21.919 and 24.159, wherein each peak may vary by ±0.5.

10. A method of treating a disease or disorder, in which aldosterone over-exposure contributes to deleterious effects of said disease or disorder in a human comprising administering an effective amount of the compound of claim 1 to said human, wherein said disease or disorder is selected from primary and secondary hyperaldosteronism, heart failure, chronic renal failure, hypertension, restenosis, obesity, nephropathy, post-myocardial infarction, renal fibrosis, and coronary heart disease.

11. A process for preparing the compound of claim 1 comprising the steps of:
   i. reacting racemic 5-(p-cyanophenyl)-5,6,7,8-tetrahydroimidazo[1,5-a]pyridine with (—)—O,O'-dibenzoyl-L-tartaric acid to form the diastereomeric (R)-(+)-5-(p-cyanophenyl)-5,6,7,8-tetrahydroimidazo[1,5-a]pyridine dibenzoyl-L-tartrate salt;
   ii. recrystallizing at least once the tartrate salt obtained in step i;
   iii. liberating the free base (R)-(+)-5-(p-cyanophenyl)-5,6,7,8-tetrahydroimidazo[1,5-a]pyridine by adding a base to a solution of the tartrate salt obtained in step ii; and
   iv. reacting said free base with phosphoric acid.

12. The compound of claim 1, wherein said compound has a selectivity for aldosterone synthase over aromatase of 100 or more, wherein said selectivity is determined by a ratio of the $IC_{50}$ values for inhibition of aromatase and aldosterone synthase and wherein the $IC_{50}$ values for inhibition of aldosterone synthase and aromatase are both measured in a NCI-H295R adrenal cell assay.

13. The crystalline compound of claim 5, wherein said crystalline compound has an X-ray powder diffraction pattern comprising 2θ values measured using CuKα radiation: 19.504; 21.919 and 24.159, wherein each peak may vary by ±0.2 degrees.

14. A pharmaceutical composition comprising a compound having the structure:

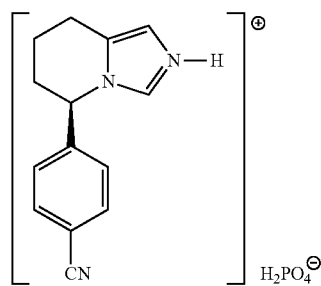

in admixture with at least one pharmaceutically acceptable excipient, wherein said compound has an enantiomeric excess of the (R) form higher than or equal to 97%.

15. The pharmaceutical composition of claim 14, wherein said pharmaceutical composition is in a tablet, pill, dispersible granule, cachet, capsule, powder, lozenge, suppository or retention enema form.

16. The method of claim 10 wherein said disease or disorder is selected from primary hyperaldosteronism and secondary hyperaldosteronism.

17. The compound of claim 1, wherein said compound has an enantiomeric excess of the (R) form higher than or equal to 98%.

18. The compound of claim 1, wherein said compound has an enantiomeric excess of the (R) form higher than or equal to 99%.

19. The compound of claim 1, wherein said compound has an enantiomeric excess of the (R) form higher than or equal to 99.5%.

20. The compound of claim 1, wherein said compound has an enantiomeric excess of the (R) form higher than or equal to 99.8%.

21. The compound of claim 1, wherein said compound has an enantiomeric excess of the (R) form higher than or equal to 99.9%.

22. The compound of claim 1, wherein said compound has less than 1% water of hydration.

23. The crystalline compound of claim 13, wherein said crystalline compound has an X-ray powder diffraction pattern comprising 2θ values measured using CuKα radiation: 19.504; 21.919; 24.159; 16.003; 26.101; 27.168; 27.542; and 29.029, wherein each peak may vary by ±0.2 degrees.

24. The pharmaceutical composition of claim 14, wherein said compound has an enantiomeric excess of the (R) form higher than or equal to 98%.

25. The pharmaceutical composition of claim 14, wherein said compound has an enantiomeric excess of the (R) form higher than or equal to 99%.

26. The pharmaceutical composition of claim 14, wherein said compound has an enantiomeric excess of the (R) form higher than or equal to 99.5%.

27. The pharmaceutical composition of claim 14, wherein said compound has an enantiomeric excess of the (R) form higher than or equal to 99.8%.

28. The pharmaceutical composition of claim 14, wherein said compound has an enantiomeric excess of the (R) form higher than or equal to 99.9%.

* * * * *